US011123543B2

(12) United States Patent
Najar

(10) Patent No.: US 11,123,543 B2
(45) Date of Patent: Sep. 21, 2021

(54) BLOOD PUMPING DEVICE

(71) Applicant: Scandinavian Real Heart AB, Västerås (SE)

(72) Inventor: Azad Najar, Västerås (SE)

(73) Assignee: SCANDINAVIAN REAL HEART AB, Västerås (SE)

( * ) Notice: Subject to any disclaimer, the term of this patent is extended or adjusted under 35 U.S.C. 154(b) by 0 days.

(21) Appl. No.: 15/501,491

(22) PCT Filed: Jul. 27, 2015

(86) PCT No.: PCT/EP2015/067135
§ 371 (c)(1),
(2) Date: Feb. 3, 2017

(87) PCT Pub. No.: WO2016/020219
PCT Pub. Date: Feb. 11, 2016

(65) Prior Publication Data
US 2017/0224894 A1   Aug. 10, 2017

(30) Foreign Application Priority Data

Aug. 7, 2014  (SE) .................................. 1450926-9
Dec. 11, 2014 (SE) .................................. 1451521-7

(51) Int. Cl.
*A61M 60/89*    (2021.01)
*A61M 60/894*   (2021.01)
(Continued)

(52) U.S. Cl.
CPC ........ *A61M 60/894* (2021.01); *A61M 1/3666* (2013.01); *A61M 60/148* (2021.01);
(Continued)

(58) Field of Classification Search
CPC .............. A61M 1/1037; A61M 1/1046; A61M 1/1049; A61M 1/1087; A61M 1/1096;
(Continued)

(56) References Cited

U.S. PATENT DOCUMENTS 4,781,716 A   11/1988 Richelsoph
4,925,377 A    5/1990 Inacio et al.
(Continued)

FOREIGN PATENT DOCUMENTS

| CN | 1377288   A | 10/2002 |
| CN | 101856520 A | 10/2010 |
| CN | 102481397 A |  5/2012 |

OTHER PUBLICATIONS

International Search Report and Written Opinion dated Oct. 22, 2015 by the International Searching Authority for Application No. PCT/EP2015/067135 on Jul. 27, 2015 and published as WO 2016/020219 on Feb. 11, 2016 (Applicant—Scandinavian Real Heart AB; Inventor—Azad Najar) (12 pages).
(Continued)

*Primary Examiner* — Christopher D. Prone
(74) *Attorney, Agent, or Firm* — Ballard Spahr LLP

(57) ABSTRACT

A blood pumping device is described having at least a first pump and a first pump actuator for inducing a blood flow in a body's circulatory system. The pump has one upper chamber having an inlet channel and one lower chamber having an outlet channel. The upper and lower chambers are separated by a movable valve plane provided with a one-way valve. The pump actuator induces movement of the valve plane in an upward and downward direction between the upper and lower chambers in response to control signals from a control unit. When the valve plane moves in an upward direction, the valve opens allowing a flow of blood from the upper to the lower chamber. The lower chamber is
(Continued)

provided with a bag-like portion forcing said flow of blood to make a turn of between 110° to 150° before leaving through the outlet channel.

18 Claims, 23 Drawing Sheets

(51) Int. Cl.
| | |
|---|---|
| *A61M 60/148* | (2021.01) |
| *A61M 60/258* | (2021.01) |
| *A61M 1/36* | (2006.01) |
| *A61M 60/40* | (2021.01) |
| *A61M 60/113* | (2021.01) |
| *A61M 60/122* | (2021.01) |
| *A61M 60/268* | (2021.01) |
| *A61M 60/896* | (2021.01) |

(52) U.S. Cl.
CPC ......... *A61M 60/258* (2021.01); *A61M 60/113* (2021.01); *A61M 60/122* (2021.01); *A61M 60/268* (2021.01); *A61M 60/40* (2021.01); *A61M 60/896* (2021.01); *A61M 2205/18* (2013.01); *A61M 2205/3331* (2013.01); *A61M 2205/3368* (2013.01); *A61M 2205/50* (2013.01); *A61M 2205/8206* (2013.01); *A61M 2205/8243* (2013.01)

(58) Field of Classification Search
CPC ......... A61M 1/10; A61M 1/12; A61B 60/892; A61B 60/894; A61B 2205/3331; A61B 2205/50; A61B 2205/8206; A61B 2205/8243
USPC .............................. 623/3.11, 3.16, 3.17, 3.19
See application file for complete search history.

(56) References Cited

U.S. PATENT DOCUMENTS

| | | | | |
|---|---|---|---|---|
| 5,108,426 | A | * | 4/1992 | Biro .................... A61M 1/1098 417/472 |
| 5,300,111 | A | * | 4/1994 | Panton ................. A61M 1/1053 623/3.19 |
| 6,669,726 | B2 | | 12/2003 | Giambruno |
| 8,535,213 | B2 | | 9/2013 | Byoung |
| 2003/0032853 | A1 | | 2/2003 | Korakianitis |
| 2004/0116769 | A1 | * | 6/2004 | Jassawalla .......... A61M 1/1046 600/16 |
| 2006/0030746 | A1 | | 2/2006 | Grossmann |

OTHER PUBLICATIONS

International Preliminary Report on Patentability dated Jul. 26, 2016 by the International Searching Authority for Application No. PCT/EP2015/067135 on Jul. 27, 2015 and published as WO 2016/020219 on Feb. 11, 2016 (Applicant—Scandinavian Real Heart AB; Inventor—Azad Najar) (26 pages).

* cited by examiner

BLOOD PUMPING DEVICE

CROSS-REFERENCE TO RELATED APPLICATIONS

The present application is a U.S. National Phase Application of International Application No. PCT/EP2015/067135, filed Jul. 27, 2015, which claims priority to Swedish Patent Application No. 1450926-9, filed Aug. 7, 2014, and Swedish Patent Application No. 1451521-7, filed Dec. 11, 2014, each of which are hereby incorporated by reference in their entirety.

TECHNICAL FIELD

The present disclosure relates to a blood pumping device such as a Total Artificial Heart (TAH) which may totally or partly replace the function of a natural heart. The disclosure also relates to a blood pumping device which may be permanently or temporarily be used as a left ventricular assist (LVAD), right ventricular assist device (RVAD) or cardiopulmonary bypass device.

BACKGROUND OF THE INVENTION

The main function of the heart in the human body is to circulate blood through the blood vessels in order to transport oxygen, nutrition, and waste products to and from body cells. Many diseases may affect the heart such as myocardial infarction, hypertension, valve insufficiency and various heart muscle diseases. The end result of such diseases may be heart failure which means that the heart has lost its ability to pump enough blood to the lungs and body tissues.

The symptoms of heart failure are shortness of breath, edema and fatigue. The only treatment option available for a patient suffering from advanced heart failure is heart transplantation. However, due to a lack of sufficient number of donor hearts the majority of advanced heart failure patients die while waiting for a heart transplant operation.

For this reason many efforts have been made during the last 50 years to develop a mechanical heart which can replace a diseased heart entirely. Until now only a few Total Artificial Hearts (TAH) i.e. mechanical hearts/heart prosthesis have been developed which have the capacity to completely replace the diseased heart. A TAH differs from a heart assist, which only assists and supports a diseased part of the heart. This means that the heart assist prosthesis operates in parallel to the patient's own heart without the need to replace the heart which is the case of the total artificial heart. Numerous heart assist prostheses exist on the market either as left ventricular assist (LVAD), right ventricular assist devices (RVAD) or biventricular assist devices.

One major complication of existing TAHs currently approved on the market is the formation of blood clots which can cause strokes, other damages, and even death when they form inside vital organs of the body as embolisms. Other complications may be bleedings and infections. These complications arise also when the TAHs are used for only a short time as a bridge when awaiting heart transplantation.

A healthy human heart normally works diligently and flawlessly throughout the lifetime of a human being without causing any complications. Therefore, in order to succeed in developing a heart prosthesis which is capable of replacing the human heart, an artificial heart is advantageously designed as a human heart. It is therefore important to understand the anatomy of the heart and how it functions physiologically. None of the existing TAHs are constructed in accordance with the physiology and anatomy of the natural human heart and this may be why none of these TAHs is able to permanently replace the function of a human heart.

A natural heart can actually be considered to consist of two pumps, the right pump and the left pump. Each pump consists of one atrium and one ventricle, thus the natural heart consists of two atria and two ventricles. The right sided pump of the heart is a low pressure system and the left sided pump is a high pressure system. De-oxygenated blood flows from the body into the right atrium, and then via the right ventricle it enters the pulmonary circulation where it is oxygenated in the lungs. Oxygenated blood flows from the pulmonary system back to the heart where it enters the left atrium, passes through the left ventricle and thereafter leaves the heart and continues into the body again.

During the last three decades the knowledge behind the function as well as how the human heart circulates blood in the body has been modified. Until recently it was believed that the heart pumps blood by means of a squeezing motion of the ventricle muscles, but this belief was modified after Stig Lundbäck and other researchers presented their research regarding the Atrioventricular (AV) plane movement as the principle way for the heart to pump blood through the vessels. The atria and the ventricles are separated by the AV plane at each side of the heart. The AV plane is equipped with valves on both the left and the right sides to prevent blood from flowing backwards in the circulatory systems. When the AV planes move downwards towards the ventricles by the contraction of the heart muscle (Myocardium) the valves are closed causing a rapid increase in pressure inside the ventricles which pushes the blood into the arteries on both the left and the right side of the heart. This piston-like function by the AV-plane gives rise to the pulsating flow of the blood which is important to maintain the function of many body organs. Thus, instead of being a squeezing pump the heart acts more like a piston pump.

A further important effect of the piston pumping principle is that it provides a continuous blood inflow to the atria without any stagnation in the two circulatory venous systems. During the downward movement of the AV-plane towards the ventricles the volume of the atrium increases and blood is drawn from the venous circulatory systems into the atria. During the subsequent upward movement of the AV-plane the valve in the AV-plane opens and blood collected inside the atrium flows to the ventricle while simultaneously allowing new blood to enter the atrium, thus creating a continuous inflow of blood into the heart while producing a pulsating outflow of blood outside the heart. This (AV) plane movement forms the underlying principle for the blood pumping device as disclosed herein.

SUMMARY OF THE INVENTION

The design of the blood pumping device as described herein is comparable to the anatomy of the natural heart which thereby enables the blood pumping device to pump blood in a manner analogous to that of the natural heart. As the blood pumping device is comparable to the natural heart physiologically, complications when using the blood pumping device as a permanent or temporary replacement for a natural heart are minimized.

In a first aspect the blood pumping device described herein contains four chambers analogous to the two atria and two ventricles of a natural heart and may advantageously be used to as total artificial heart (TAH) implant and completely replace a diseased heart in a subject in need thereof. The four-chambered blood pumping device may also be used as a pulsatile circulatory support device to temporarily take over the function of a heart during heart surgery on a subject or alternatively as a bi-ventricular assist device (Bi-VAD) to partially or completely replace the function of a failing heart.

In a first aspect a four-chambered blood pumping device comprising at least a first and a second pump and a first and second pump actuating means for inducing a blood flow in a body's vascular system is disclosed. Each pump comprises one upper chamber having an inlet channel and one lower chamber having an outlet channel.

The upper and lower chambers in a pump correspond to the atrium and the ventricle of the natural heart. The upper and lower chambers in each pump are separated by a movable valve plane provided with a valve. The valve plane corresponds to the atrioventricular (AV) plane (i.e. the plane of fibrous tissue) between the atria and ventricles of a natural heart. Advantageously the first pump and the second pump are identical and the valves provided in the valve planes of each pump correspond to the mitral valve on the left side of the natural heart and the tricuspid valve on the right side. The valve plane divides the inside of the pump in two compartments or chambers, one upper chamber and one lower chamber. The chambers are advantageously of a biocompatible material such as e.g. silicone, polyurethane, titanium, ceramics, Polytetrafluoroethylene (PTFE) coated metal, diamond coated metal or a combination thereof.

The pump actuating means are configured to actuate a movement of said valve planes in an upward and downward direction between said upper and lower chambers in response to control signals from a control unit, such that when said valve planes move in an upward direction, the valves provided in the valve planes are in an open position allowing a flow of blood from the upper chambers to the lower chambers, and when the valve planes moves in a downward direction the valves are in the closed position and blood is ejected from the lower chambers through the outlet channels.

In order to simulate the shape of a natural heart, the inside bottom part of the lower chamber is provided with a bag-like portion. The ventricles of a natural heart have a design which enables the blood to hit a stopping surface at the level of the apex before leaving the ventricles. The internal structure of the ventricle has a sharp turn at the bottom of the ventricle i.e. at the apex of a natural heart, which forms a bend of approximately 110-150°. This means that when blood reaches the bottom of the apex it hits a stopping surface and the kinetic energy stored in the flowing blood which has flooded into the ventricle from the atrium through the open valve, is for a short moment transmitted to the heart and thereafter transmitted back to the blood when the AV plane moves downward and pushes the blood from the ventricle. Next the blood leaves the heart through the aortic and pulmonary valves and continues into the aorta or the pulmonary arteries.

The stopping surface at the abrupt bend inside the ventricle at the apex makes the heart use less energy than expected considering that it has to pump a large volume of blood throughout the complete circulatory system. Most of the kinetic energy which is stored in the blood when it is in motion is transferred to the heart when the speed of blood moving from atrium to ventricles decelerates and is stopped when the blood hits the sharp bend at the stopping surface at the apex inside the ventricle. This kinetic energy is transferred back to the blood again when the AV plane moves towards the ventricle to pump blood through the aortic and pulmonary valve to the major arteries. Thus, there is an amount of energy which is transferred from the blood to the heart and again back to the blood at the bend inside the ventricle at the apex. At the same time the deceleration and acceleration in the flow of blood inside the ventricle create a dynamic flow of blood preventing the formation of blood clots.

In the four-chambered blood pumping device as described herein the bag-like design of the lower chambers mimics the design of the apex of a natural heart such that at the bottom of the lower chambers the blood flow comes to a sudden stop and changes direction abruptly. The turn at the inside of the bag-like portion at the bottom of the lower chambers forms a sharp bend of approximately 90-340°, more preferably between 100-300°, more preferably between 105-200°, and most preferably a bend between 110-150°, which is similar to the bend inside the ventricle of a natural heart. Thereafter the blood continues into the outlet channels and subsequently passes through the outlet valves and into the major arteries.

The cross sections of the lower chambers and the bag-like portions at the bottom part of the lower chambers advantageously have a triangular shape. When used herein the term "a triangular shape" comprises modified triangular shapes, in particular shapes having rounded corners and preferably slightly curved sides. A triangular shape enables an optimal flow of the blood after entering the lower chamber through the valve located in the valve plane of the internal cylinder and when it continues into the bag-like portion of the lower chamber, and thereafter into the outlet channel. As in a natural heart, a triangular shaped cross-section facilitates the formation of several channels inside the cavity of the lower chamber to allow the blood to hit a stopping surface at the bottom part of the bag-like shape in the lower chamber from different angles before it changes direction and exits through the outlet channel. The formation of channels inside the triangular cross sectional area may also prevent different blood flows from colliding with each other. The cross-sections of the lower chambers and the bag-like portions at the bottom part of the lower chambers may also have an oval shape or a circular shape.

The inner walls of the lower chambers, as well as the outlet channels, may be provided with rough surfaces to simulate the trabeculae carneae i.e. the muscular ridges that crisscross and project from the inner walls of the ventricles of a natural heart. A rough surface minimizes the formation of eddies in the blood flow next to the wall of the lower chamber much like when water flows past an obstacle in a river. With a flat chamber wall the moving blood creates multiple swirls of blood close to the wall surface. These blood swirls run opposite to the main blood stream disrupting the flow and decreasing the speed of blood inside the lower chamber. A rough surface on the inside of the lower chambers and outlet channels will therefore minimize the formation of blood swirls and further increase the speed of blood inside the lower chambers of the four-chambered blood pumping device.

The outlet of the ventricle in a natural heart has a diameter which decreases continuously towards the aorta or the pulmonary artery. Advantageously, the outlet channels from the lower chambers may also have a diameter which decreases continuously similarly to the design of the outlet of a ventricle in a natural heart. A rough inner surface together with a decreasing diameter of the outlet channel will significantly increase the speed of the blood flow exiting the lower chamber of the four-chambered blood pumping device.

In order for the four-chambered blood pumping device to be able to circulate the blood in a leak-free manner, the inside of the upper and lower chambers are provided with a flexible lining material made from plastic or rubber. The flexible membrane may also be comprised of two or more layers of membrane material to improve its strength. The flexible lining material is advantageously made from a biocompatible material like silicone, polyurethane or another biocompatible material.

The outlet channels of the four-chambered blood pumping device are provided with outlet valves to prevent the return of blood back into the lower chamber after the blood has been ejected through the outlet channel. The outlet channel valves correspond to the aortic valve or the pulmonary valve respectively of the natural heart.

Each pump of the four-chambered blood pumping device may further comprise one internal cylinder provided with a valve plane, and one external cylinder, wherein the internal cylinder is movably arranged inside the external cylinder. In this embodiment the upper and lower chambers which are separated by the valve plane are housed partially inside the internal cylinder. The upper part of the internal cylinder forms the upper chamber corresponding to an atrium of the natural heart, and the lower part of the internal cylinder forms the lower chamber and corresponds to a ventricle of the natural heart. The valve plane is arranged in the internal cylinder, such that the valve plane divides the internal cylinder into two parts, one upper part and one lower part. The valve plane corresponds to the atrioventricular (AV) plane (i.e. the plane of fibrous tissue) between the atria and ventricles of a natural heart.

The internal cylinders with the valve planes are movably arranged inside the external cylinders. Pump actuating means are configured to apply a movement to said internal cylinders in an upward and downward direction in response to control signals from a control unit such that when the internal cylinders move in an upward direction inside the external cylinders, the valves provided in the valve planes are in an open position allowing a flow of blood from the upper chambers to the lower chambers, and when the internal cylinders move in a downward direction inside the external cylinders the valves are in the closed position and blood is ejected from the lower chambers through the outlet channels.

The internal and external cylinders are advantageously made from a stiff material, such as e.g. a biocompatible material such as, aluminum, titanium, or ceramics, Polytetrafluoroethylene (PTFE) coated metal, diamond coated metal, silicone or polyurethane coated metals or a combination thereof.

To achieve an effective pumping function of the four-chambered blood pumping device, it is essential that the internal cylinders move in a leak-free manner during their movement inside the external cylinders. Therefore the fitting of the internal cylinders inside the external cylinders, is advantageously made leak-free by providing the insides of the upper and lower chambers with a flexible lining material made from plastic or rubber. The flexible lining material is advantageously made from a biocompatible material like silicone, polyurethane or another biocompatible material. The flexible membrane may also be comprised of two or more layers of membrane material to improve its strength.

To achieve an effective and energy efficient operation of the four-chambered blood pumping device, it is essential that the internal cylinders move in a virtually friction-less manner inside the external cylinders. The outer walls of the internal cylinders as well as the inner walls of the external cylinders are preferably separated from each other or provided with gliding surfaces. The gliding surfaces are advantageously made from e.g. a ceramic material, titanium, steel, carbon fiber or any other material that will enable the internal cylinders to move inside the external cylinder in an essentially friction-free manner.

The pump actuating means may advantageously be a driving cylinder provided with an external cogwheel, wherein the external cogwheel is arranged to cooperate with a motor cogwheel of an electromechanical motor such that when the electromechanical motor rotates the motor cogwheel, said motor cogwheel cooperates with the external cogwheel on the driving cylinder and rotates the driving cylinder.

The upward and downward movement of the internal cylinders may in this case advantageously be realized by means of internal screw threads provided on the driving cylinders which in turn are arranged to cooperate with external screw threads provided on the outer surfaces of the internal cylinders The driving cylinders encircle the internal cylinders such that when the driving cylinders rotate, a cooperative arrangement between the internal screw threads on the inside walls of the driving cylinders and the external screw threads on the outer surfaces of the internal cylinders, enable a linear up- and down-movement of the internal cylinders inside the external cylinders, which results in a pumping action of the pumps. The upward or downward movement depends on whether the rotational movement of the driving cylinders is in a clock-wise or a counter clock-wise direction.

In another embodiment the rotation of the driving cylinder and subsequently the upward and downward movement of the internal cylinders may be realized by means of stator cylinders with an integrated stator coil. The stator coil is fixed to a stator cylinder which is connected to the external cylinder to prevent the stator cylinder from rotating. The stator cylinder encircles the driving cylinders. One or more permanent magnets are embedded and integrated with the outer surface of the driving cylinder to enable the internal cylinder to rotate when an electrical current is applied through the stator coil. In this embodiment the entire driving cylinder functions as a rotor in an electromechanical motor and thus the stator cylinder together with the driving cylinder works as an electromechanical motor The pump actuating means may advantageously be a cylinder actuating assembly connected to the internal cylinder and powered by means of a motion generator to enable a linear up-and-down motion of the internal cylinder inside the external cylinder.

The cylinder actuating assembly is provided with arms which extend around at least part of the external cylinder and said arms connect to opposite sides of the internal cylinder through rectangular shaped openings in the wall of the external cylinder. Preferably the arms reach at least half way around the circumference of the external cylinder. The cylinder actuating assembly is powered by a motion generator to enable the movement of the internal cylinder in an up-and-down movement inside the external cylinder. Advantageously the up-and-down movement of the cylinder actuating assembly is stabilized by at least two stabilizing members located on the arms of the cylinder actuating assembly. Advantageously said stabilizing members are made from a friction-less material such as ceramics, ceramics, Polytetrafluoroethylene (PTFE) coated metal like titanium or diamond coated metal (titanium), to enable a friction-less up-and-down movement of the cylinder actuating assembly.

The motion generator powers the up-and-down movement of the cylinder actuating assembly. It is important that the motion generator is capable of providing a stable and reliable motion of the cylinder actuating assembly at a steady pace. Advantageously, the motion generator may be a ball screw or a roller screw which translates a rotational motion provided by a power source into a linear up-and-down motion of the internal cylinders inside the external cylinders.

Ball screws or roller screws are mechanical linear actuators that translate rotational motion to linear motion with little friction. In a ball screw a threaded shaft provides a helical raceway for ball bearings which act as a precision screw. They are made to close tolerances and are therefore suitable for use in situations in which high precision is necessary. The ball assembly acts as the nut while the threaded shaft is the screw. A roller screw is a mechanical actuator similar to a ball screw that uses rollers as the load transfer elements between nut and screw instead of balls. The rollers are typically threaded but may also be grooved depending on roller screw type. Providing more bearing points than ball screws within a given volume, roller screws can be more compact for a given load capacity while providing similar efficiency (75%-90%) at low to moderate speeds, and maintain relatively high efficiency at high speeds.

The three main elements of a typical roller screw are the screw shaft, nut and roller. The screw, a shaft with a multi-start V-shaped thread, provides a helical raceway for multiple rollers radially arrayed around the screw and encapsulated by a threaded nut. The thread of the screw is typically identical to the internal thread of the nut. The rollers spin in contact with, and serve as low-friction transmission elements between screw and nut. The rollers typically have a single-start thread with convex flanks that limit friction at the rollers' contacts with screw and nut. As with a lead screw or ball screw, rotation of the nut results in screw travel, and rotation of the screw results in nut travel.

In this embodiment the nut of the ball or roller screw is advantageously an integrated part of the cylinder actuating assembly. The nut of the ball or roller screw forms the base from which the two arms of the cylinder actuating assembly extend around at least part of the circumference of the external cylinder to connect to opposite sides of the internal cylinder through rectangular shaped openings in the wall of the external cylinder. The screw of the ball or roller screw is advantageously provided with a cogwheel in a cooperative arrangement with a motor cogwheel of a power source, such as e.g. an electromechanical motor. When the power source rotates the motor cogwheel, said motor cogwheel cooperates with a cogwheel provided on the screw of the ball or roller screw and rotates said screw. When the screw rotates, its rotational movement is translated into a linear movement of the cylinder actuating assembly i.e. the nut with the arms which moves in an upward direction or a downward direction depending on the direction of rotation of the electromechanical motor. Each pump contains a pump actuating means and both pumps of the heart operate simultaneously and in the same direction.

In an alternative embodiment the motion generator may be a hydraulic or pneumatic pumping system which when connected to the internal cylinder by means of a cylinder actuator enables the up-and-down movement of the internal cylinder inside the external cylinder.

A hydraulic cylinder (also called a linear hydraulic motor) is a mechanical actuator that is used to give a unidirectional force through a unidirectional stroke. Hydraulic cylinders get their power from pressurized hydraulic fluid, which is typically oil. The hydraulic cylinder consists of a cylinder barrel, in which a piston connected to a piston rod moves back and forth. The barrel is closed on one end by the cylinder bottom (also called the cap) and the other end by the cylinder head (also called the gland) where the piston rod comes out of the cylinder. The piston has sliding rings and seals. The piston divides the inside of the cylinder into two chambers, the bottom chamber (cap end) and the piston rod side chamber (rod end/head end).

Pneumatic cylinders (sometimes known as air cylinders) are mechanical devices which use the power of compressed gas to produce a force in a reciprocating linear motion. Like hydraulic cylinders, something forces a piston to move in the desired direction. The piston is a disc or cylinder, and the piston rod transfers the force it develops to the object to be moved.

In this embodiment hydraulic or pneumatic cylinder rods of the hydraulic or pneumatic pumping systems are directly connected to the cylinder actuating assemblies and enable the linear up-and-down movements of the cylinder actuating assemblies. The two arms of the cylinder actuating assembly extend around at least part of the circumference of the external cylinder to connect to opposite sides of the internal cylinder through rectangular shaped openings in the wall of the external cylinder. When the hydraulic or pneumatic cylinder operates, i.e. when the piston rod inside the hydraulic or pneumatic cylinders moves in and out, the cylinder actuating assembly moves simultaneously with the piston rod and thereby enables the up-and-down movement of the internal cylinder inside the external cylinder. Each pump contains a pump actuating means and both pumps of the heart operate simultaneously and in the same direction.

The four-chambered blood pumping device may also for safety reasons be provided with at least one additional pump actuating means which functions independently of the first and second pump actuating means. The additional pump actuating means may be identical or a simpler version of the first and second pump actuating means. It is advantageously designed to passively follow the pace of the first and second pump actuation means. However, in case of failure of the first and/or second pump actuating means, the additional pump actuating means will immediately become activated and take control of the blood pumping activity until the necessary medical assistance can be provided. Advantageously an alarm system immediately alerts when the first and/or second pump actuating means show signs of failure, and the necessary steps to remedy any problems may be commenced without delay.

In one aspect the four-chambered blood pumping device may be used as a Total Artificial Heart (TAH) Implant replacing a natural heart in a subject. As used herein the term "subject" refers to a living animal or human in need of treatment for, or susceptible to, a condition involving a heart disease. The term subject includes, but is not limited to, humans, nonhuman primates such as chimpanzees and other apes and monkey species, farm animals such as cattle, sheep, pigs, goats and horses, domestic mammals such as dogs and cats, laboratory animals including rodents such as mice, rats and guinea pigs, and the like. The term does not denote a particular age or sex. Thus, adult and newborn subjects, as well as fetuses, whether male or female, are intended to be covered. In preferred embodiments, the subject is a mammal, including humans and non-human mammals. In the most preferred embodiment, the subject is a human.

After the natural heart has been removed from a subject the outlet and inlet channels of the four-chambered blood pumping device are connected to the natural blood vessels which normally enter and exit the heart by a standard vessel graft. The vessel graft is advantageously connected to the vessels by suturing and to the inlet/outlet channels of the four-chambered blood pumping device by means of fast connections or gluing. When implanted inside the body of a subject, the four-chambered blood pumping device is supported by the ribs and the sternum and advantageously fastened thereto by suturing or wiring.

The energy to power the pump actuating means may be supplied by an external source via a cable through the skin, or alternatively by an implanted battery. The implanted battery may be recharged from the outside via a cable or by means of induction or ultra sound.

The pump actuating means are advantageously controlled by an implanted micro-computer or electronic chips. The input information to the computer is advantageously provided from the sinus node, which remains inside the body after removing the diseased heart, via pacemaker-type electrodes. However, the micro-computer or electronic chips may also receive signals from pressure sensors placed around major arteries. When the patient changes his physical activities the blood pressure will reflect the situation. The micro-computer or the electronic chips will send information to the pump actuating means to change its pumping activity accordingly. If for some reason the micro-computer or electronic chips are not receiving any input information, the pump actuating means will continue at a constant level of activity, and instead the patient will have to adjust his physical activities. The body temperature, which increases with physical activity, may also be used to activate the pump actuating means during high physical efforts.

In a further aspect the four-chambered blood pumping device may be used temporarily as an extracorporeal circulation support system during e.g. open heart surgery for some hours, or for some days e.g. when the heart needs to recover from an acute disease. In this alternative the extracorporeal circulation support system works as a cardiac bypass pulsatile pump. The natural lungs in a subject oxygenate the blood as usual. The outlet and inlet channels of the four-chambered blood pumping device are connected to the natural blood vessels which normally enter and exit the heart by a standard vessel graft. The vessel graft is advantageously connected to the vessels by suturing and to the inlet/outlet channels of the four-chambered blood pumping device by means of fast connections or gluing.

Instead of connecting vessel grafts to the lung veins or the superior or inferior vena cava, vessel grafts are advantageously connected or sutured directly to the atria or the ventricles. The inlet channels to the upper chambers of the blood pumping device are connected to the vessel graft from the atria or the ventricles draining blood from the natural heart directly to the upper chambers of the four chambered blood pumping device. Oxygenated blood is drained from the left atrium or ventricle into the inlet channel of the upper chamber of the first pump. Deoxygenated blood is drained from the right atrium or ventricle into the inlet channel of the upper chamber of the second pump.

Vessel grafts are easily sutured to the aorta and the pulmonalis, each of which are connected to the outlet channels of the lower chambers.

In a further aspect of the invention only one pump of the blood pumping device as described above may advantageously be used under certain circumstances.

Thus, a second aspect the blood pumping device described herein contains two chambers analogous to the one atrium and one ventricle of a natural heart and may advantageously be used as a pulsatile circulatory support device to temporarily take over the function of a heart during heart surgery on a subject or alternatively as a left ventricular assist device (LVAD) or right ventricular assist device (RVAD) to partially or completely replace the function of a failing heart, or when one side of the heart is failing.

A further aspect of the invention therefore relates to a blood pumping device comprising one pump and at least a first pump actuating means for inducing a blood flow in a body's vascular system. The pump comprises one upper chamber having an inlet channel and one lower chamber having an outlet channel.

The two chambers correspond to the atrium and the ventricle of the natural heart and the upper and lower chambers are separated by a movable valve plane provided with a valve. The valve plane corresponds to the atrioventricular (AV) plane (i.e. the plane of fibrous tissue) between the atria and ventricles of a natural heart. A valve is provided in the valve plane of the pump. Said valve corresponds to the mitral valve in a natural heart if the two-chambered blood pumping device is used as a LVAD, and to the tricuspid valve if the two-chambered blood pumping device is used as a RVAD. The valve plane divides the inside of the pump in two parts or chambers, one upper part (chamber) and one lower part (chamber). The chambers are advantageously of a biocompatible material such as, titanium, ceramics, Polytetrafluoroethylene (PTFE) coated metal, or diamond coated metal, or any other biocompatible materials.

The pump actuating means is configured to actuate a movement of said valve plane in an upward and downward direction between said upper and lower chambers in response to control signals from a control unit, such that when said valve plane moves in an upward direction, the valve provided in the valve plane is in an open position allowing a flow of blood from the upper chamber to the lower chamber, and when the valve plane moves in a downward direction the valve is in the closed position and blood is ejected from the lower chamber through the outlet channel.

The inside bottom part of the lower chamber is provided with a bag-like portion which mimics the design of the apex of a natural heart such that at the bottom of the chamber the blood flow comes to a sudden stop and changes direction abruptly. The turn at the inside of the bag-like portion at the bottom of the lower chamber forms a sharp bend of approximately 90-340°, more preferably between 105-300°, more preferably between 105-200°, and most preferably a bend between 110-150°, which is similar to the bend inside the ventricle of a natural heart. Thereafter the blood continues into the outlet channel and subsequently passes through the outlet valve and into the major arteries. The advantages of the bend at the bottom of the lower chamber regarding the blood flow inside the two-chambered blood pumping device is explained above in connection with the four-chambered heart.

The cross section of the lower chamber and the bag-like portion at the bottom part of the lower chamber advantageously has a triangular shape. When used herein the term "a triangular shape" comprises modified triangular shapes, in particular shapes having rounded corners and preferably slightly curved sides. The advantages of the triangular shaped cross section of the lower chamber and the bag-like portion is described above in connection with the four-chambered heart. The cross-section of the lower chamber and the bag-like portion at the bottom part of the lower chamber may also have an oval shape or a circular shape.

The inner walls of the lower chamber, as well as in the outlet channel, may be provided with a rough surface to simulate the trabeculae carneae i.e. the muscular ridges that crisscross and project from the inner walls of the ventricles of a natural heart. The advantage of providing the lower chamber and the outlet channel with a rough surface is described above in connection with the four-chambered heart. The outlet channel from the lower chamber may also have a diameter which decreases continuously similarly to the design of the outlet of a ventricle in a natural heart. A rough inner surface together with a decreasing diameter of the outlet channel will significantly increase the speed of the blood flow exiting the lower chamber of the two-chambered blood pumping device.

In order for the two-chambered blood pumping device to be able to circulate blood in a leak-free manner the insides of the upper and lower chambers are provided with a flexible lining material made from plastic or rubber. The flexible membrane may also be comprised of two or more layers of membrane material to improve its strength. The flexible lining material is advantageously made from a biocompatible material like silicone, polyurethane or another biocompatible material.

The outlet channel of the two-chambered blood pumping device is provided with an outlet valve to prevent the return of blood back in to the lower chamber after the blood has been ejected through the outlet channel. The outlet channel corresponds to the aortic or pulmonary valves of the natural heart.

The pump of the two-chambered blood pumping device may further comprise one internal cylinder provided with a valve plane, and one external cylinder, wherein the internal cylinder is movably arranged inside the external cylinder. In this embodiment the upper and lower chambers separated by the valve plane are partially housed inside the internal cylinder. The upper part of the internal cylinder forms the upper chamber corresponding to an atrium of the natural heart, and the lower part of the internal cylinder forms the lower chamber and corresponds to a ventricle of the natural heart. The valve plane is arranged inside the internal cylinder, such that the valve plane divides the internal cylinder in two parts, one upper part and one lower part. The valve plane corresponds to the atrioventricular (AV) plane (i.e. the plane of fibrous tissue) between the atria and ventricles of a natural heart.

The internal cylinder with the valve plane is movably arranged inside the external cylinder. A pump actuating means is configured to actuate a movement of said internal cylinder in an upward and downward direction in response to control signals from a control unit such that when the internal cylinder moves in an upward direction inside the external cylinder, the valve provided in the valve plane is in an open position allowing a flow of blood from the upper chamber to the lower chamber, and when the internal cylinder moves in a downward direction inside the external cylinder the valve is in the closed position and blood is ejected from the lower chamber through the outlet channel.

The internal and external cylinders are advantageously made from a stiff material, such as e.g. a biocompatible material such as titanium, ceramics, Polytetrafluoroethylene (PTFE) coated metal, diamond coated metal, silicone or polyurethane coated metals or a combination thereof.

To achieve an effective pumping function of the two-chambered blood pumping device, it is essential that the internal cylinder moves in a leak-free manner during its movement inside the external cylinder. Therefore the fitting of the internal cylinder inside the external cylinder, is advantageously made leak-free by providing the inside of the upper and lower chambers with a flexible lining material made from plastic or rubber. The flexible lining material is advantageously made from a biocompatible material like silicone, polyurethane or another biocompatible material. The flexible membrane may also be comprised of two or more layers of membrane material to improve its strength.

To achieve an effective and energy efficient operation of the two-chambered blood pumping device, it is essential that the internal cylinder moves in a virtually friction-less manner inside the external cylinder. The outer walls of the internal cylinder as well as the inner walls of the external cylinder are preferably separated from each other or provided with gliding surfaces. The gliding surfaces are advantageously made from e.g. a ceramic material, titanium, steel, carbon fiber or any other material that will enable the internal cylinders to move inside the external cylinder in an essentially friction-free manner.

The pump actuating means may advantageously be a cylinder actuating assembly connected to the internal cylinder and powered by means of a motion generator to enable a linear up-and-down motion of the internal cylinder inside the external cylinder.

The cylinder actuating assembly is provided with arms which extend around at least part of the external cylinder and said arms connect to opposite sides of the internal cylinder through rectangular shaped openings in the wall of the external cylinder. Preferably the arms reach at least half way around the circumference of the external cylinder. The cylinder actuating assembly is powered by a motion generator to enable the movement of the internal cylinder in an up-and-down movement inside the external cylinder. Advantageously the up-and-down movement of the cylinder actuating assembly is stabilized by at least two stabilizing members located on the arms of the cylinder actuating assembly. Advantageously said stabilizing members are made from a friction-less material such as ceramics, Polytetrafluoroethylene (PTFE) coated metal like titanium or diamond coated metal (titanium), to enable a friction-less up-and-down movement of the cylinder actuating assembly.

The motion generator powers the up-and-down movement of the cylinder actuating assembly. It is important that the motion generator is capable of providing a stable and reliable motion at a steady pace.

Advantageously, the motion generator may be a ball screw or a roller screw which translates a rotational motion provided by a power source into a linear up-and-down motion of the internal cylinder inside the external cylinder. The function of ball or roller screws are described above in connection with the four-chambered blood pumping device.

In this embodiment the nut of the ball or roller screw advantageously is an integrated part of the cylinder actuating assembly. The nut of the ball or roller screw forms the base from which the two arms of the cylinder actuating assembly extend around at least part of the circumference of the external cylinder to connect to opposite sides of the internal cylinder through rectangular shaped openings in the wall of the external cylinder. The screw of the ball or roller screw is advantageously provided with a cogwheel in a cooperative arrangement with a motor cogwheel of power source, such as e.g. an electromechanical motor. When the power source rotates the motor cogwheel, said motor cogwheel cooperates with a cogwheel provided on the screw of the ball or roller screw and rotates said screw. When the screw rotates, its rotational movement is translated into a linear movement of the cylinder actuating assembly i.e. the nut with the arms which moves in an upward direction or a downward direction depending on the direction of rotation of the electromechanical motor.

In an alternative embodiment the motion generator may be a hydraulic or pneumatic pumping system which when connected to the internal cylinder by means of a cylinder actuator enables the up-and-down movement of the internal cylinder inside the external cylinder. The function of hydraulic or pneumatic cylinders is described above in connection with the four-chambered blood pumping device.

In this embodiment the hydraulic or pneumatic cylinder piston rods of the hydraulic or pneumatic pumping systems are directly connected to the cylinder actuating assembly and enable the linear up-and-down movement of the cylinder actuating assembly. The two arms of the cylinder actuating assembly extend around at least part of the circumference of the external cylinder to connect to opposite sides of the internal cylinder through rectangular shaped openings in the wall of the external cylinder. When the hydraulic or pneumatic cylinder operate, i.e. when the piston rod inside the hydraulic or pneumatic cylinders moves in and out, the cylinder actuating assembly moves simultaneously with the piston rod and thereby enables the up-and-down movement of the internal cylinder inside the external cylinder.

The pump actuating means may advantageously be a driving cylinder provided with an external cogwheel, said external cogwheel is arranged to cooperate with a motor cogwheel of an electromechanical motor such that when the electromechanical motor rotates the motor cogwheel, said motor cogwheel cooperates with the external cogwheel on the driving cylinder and rotates the driving cylinder.

The upward and downward movement of the internal cylinder may in this case advantageously be realized by means of an internal screw thread provided on the driving cylinder which in turn is arranged to cooperate with an external screw thread provided on the outer surface of the internal cylinder. The driving cylinder encircles the internal cylinder such that when the driving cylinder rotates, a cooperative arrangement between the internal screw thread on the inside wall of the driving cylinder and the external screw thread on the outer surface of the internal cylinder, enables a linear up- and down-movement of the internal cylinder inside the external cylinder, which results in a pumping action of the pump. The upward or downward movement depends on whether the rotational movement of the driving cylinder is in a clock-wise or a counter clockwise direction.

In another embodiment the rotation of the driving cylinder and subsequently upward and downward movement of the internal cylinders may be realized by means of stator cylinders with an integrated stator coil. The stator coil is fixed to a stator cylinder which is connected to the external cylinder to prevent the stator cylinder from rotating. The stator cylinder encircles the driving cylinder. One or more permanent magnets are embedded and integrated with the outer surface of the driving cylinder to enable the internal cylinder to rotate when an electrical current is applied through the stator coil. In this embodiment the entire driving cylinder functions as a rotor in an electromechanical motor and thus the stator cylinder together with the driving cylinder works as an electromechanical motor.

The two-chambered blood pumping device may also for safety reasons be provided with at least one additional pump actuating means which functions independently of the first pump actuating means. The additional pump actuating means may be identical or simpler versions of the first pump actuating means. It is advantageously designed to passively follow the pace of the first pump actuating assembly. However, in case of failure of the first pump actuating means, the additional pump actuating means will immediately become activated and take control of the blood pumping activity until the necessary medical assistance can be provided. Advantageously an alarm system immediately alerts when the first pump actuating means shows signs of failure, and the necessary steps to remedy any problems may be commenced without delay.

In a further aspect of the invention the two-chambered blood pumping device relates to a ventricular assist device (VAD). A VAD is a mechanical pump that's used to support heart function in a subject who has a partially diseased heart, such as e.g. a malfunctioning ventricle. The device takes blood from a diseased ventricle of the heart and helps pump it to the aorta if the diseased part of the heart is the left ventricle, or to the pulmonary artery if the diseased ventricle is the right ventricle. A VAD may be used if one or both of the ventricles don't work well because of heart disease. A VAD can help support the ventricle temporarily until the diseased ventricle recovers or permanently as a distention therapy if recovery of the diseased ventricle is not expected. The VAD could also be used as bridge to transplantation until the subject receives a transplanted heart. The term subject is explained elsewhere in this document.

In one aspect the two-chambered blood pumping device may be used as a left ventricular assist device (LVAD) for implantation in a subject suffering from heart disease affecting the function of the left ventricle. The LVAD helps the left ventricle to pump blood to the aorta.

In a further aspect of the invention the two-chambered blood pumping device may be used as a right ventricular assist device (RVAD) for implantation in a subject suffering from heart disease affecting the function of the right ventricle. The RVAD helps the right ventricle to pump blood to the pulmonary artery.

The inlet channel of the two chambered blood pumping device is connected to vessels which normally enter and exit the heart by a standard vessel graft. The vessel graft is connected to the vessels either by fast connection or by suturing. The graft may be connected to the outlet and/or inlet channels by means of blocking stripes made from glass fiber reinforced silicone or other material used for this purpose. The energy to power the pump actuating means may be supplied by an external source via a cable through the skin, or alternatively by an implanted battery. The implanted battery may be recharged from the outside via a cable or by means of induction or ultra sound.

The pump actuating means is advantageously controlled by an implanted micro-computer or electronic chips. The input information to the computer is advantageously provided from the sinus node via pacemaker-type electrodes. However, the micro-computer or electronic chips may also receive signals from pressure sensors placed around major arteries. When the patient changes his physical activities the blood pressure will reflect the situation. The micro-computer or the electronic chips will send information to the pump actuating means to change its pumping activity accordingly. If for some reason the micro-computer or electronic chips are not receiving any input information, the pump actuating means will continue at a constant level of activity, and instead the patient will have to adjust his physical activities. The body temperature, which increases with physical activity, may also be used to activate the pump actuating means during high physical efforts.

When implanted inside the body of a subject, the two-chambered blood pumping device is supported by the ribs and the sternum and advantageously fastened thereto by suturing or wiring.

In a further aspect the two-chambered blood pumping device may be used as a cardiopulmonary bypass (CPB) complementary pump during surgery on a subject. Operations involving the opening of the heart chambers require the use of a CPB to support the essential circulation of the blood in the body during that period. A CPB mechanically circulates and oxygenates blood for the body while bypassing the heart and lungs. The CPB enables perfusion of blood to other body organs while the surgeon works in a bloodless surgical field.

The CPB pump itself is often referred to as a heart-lung machine. CPB is a form of extracorporeal circulation. The disadvantage of this technique is that in the cardiopulmonary bypass the blood pumps back to the body continuously. The continuous blood flow has disadvantages for the functions of the vital organs of the body, especially the kidneys and the brain which will limit the connections period of Cardiopulmonary bypass to the circulation to few hours and thereby limit the surgical time, Typically, when using the Heart-Lung machine, blood is drained by placing a cannula in right atrium, vena cava, or femoral vein to a reservoir, and returned oxygenated to the cannulated arterial system by utilizing a roller pump and artificial lung (oxygenator or gas-exchanger). The cannula which used to return the oxygenated blood is usually inserted in the ascending aorta, but it may also be inserted in the femoral artery.

The two-chambered blood pumping device as disclosed herein may advantageously be used with already existing cardiopulmonary bypass technique to alter a continuous blood flow to pulsatile blood flow. The two-chambered blood pumping device can be used in a routine CPB (cardiopulmonary bypass) to achieve pulsatility and thereby as such to get all positive physiological effect especially on the kidneys and brain. A CPB unit comprises an expandable rexpanda, the two-chambered blood pumping device, a blood filter and a security shunt system. The CPB unit is inserted in the arterial line of the CPB

BRIEF DESCRIPTION OF THE DRAWINGS

FIGS. 3a-c show different advantageous cross sectional shapes of the bag-like portion of the lower chamber.

DETAILED DESCRIPTION

Blood Pumping Device with Four Chambers

Figure 1:
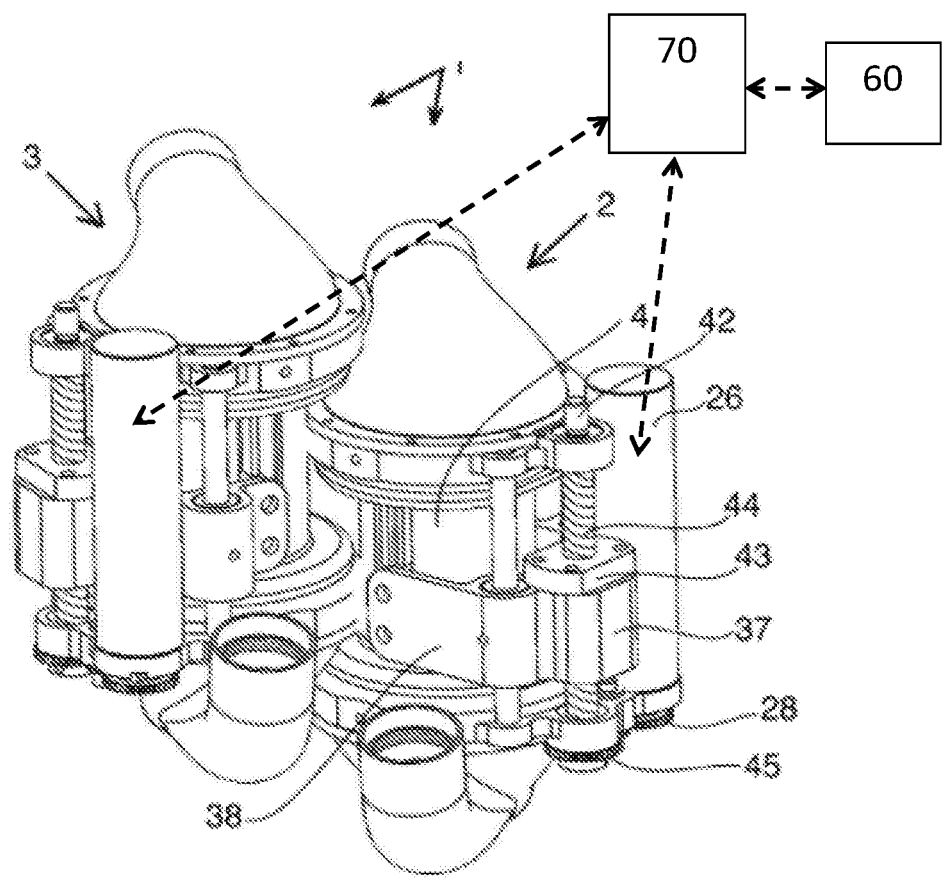
FIG. 1 is a view of a four-chambered blood pumping device as described herein.

A blood pumping device 1 having four chambers is disclosed in FIG. 1. The four-chambered blood pumping device 1 comprises two pumps, a first pump 2 and a second pump 3, and a first and second pump actuating means for inducing a blood flow in a body's circulatory system. The first and the second pumps 2, 3 are identical in their construction and the general design of a pump of the four-chambered blood pumping device 1 will now be described in detail.

Figure 2:
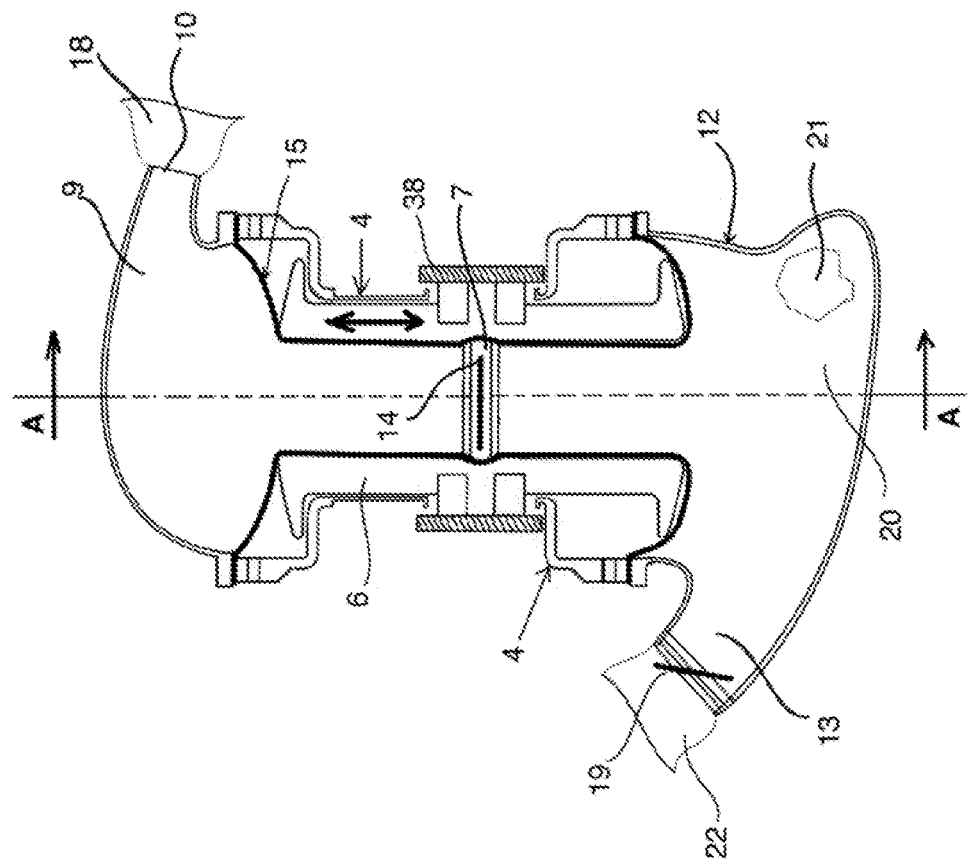
FIG. 2 shows cross sectional views of the four-chambered blood pumping device.
Figure 2:
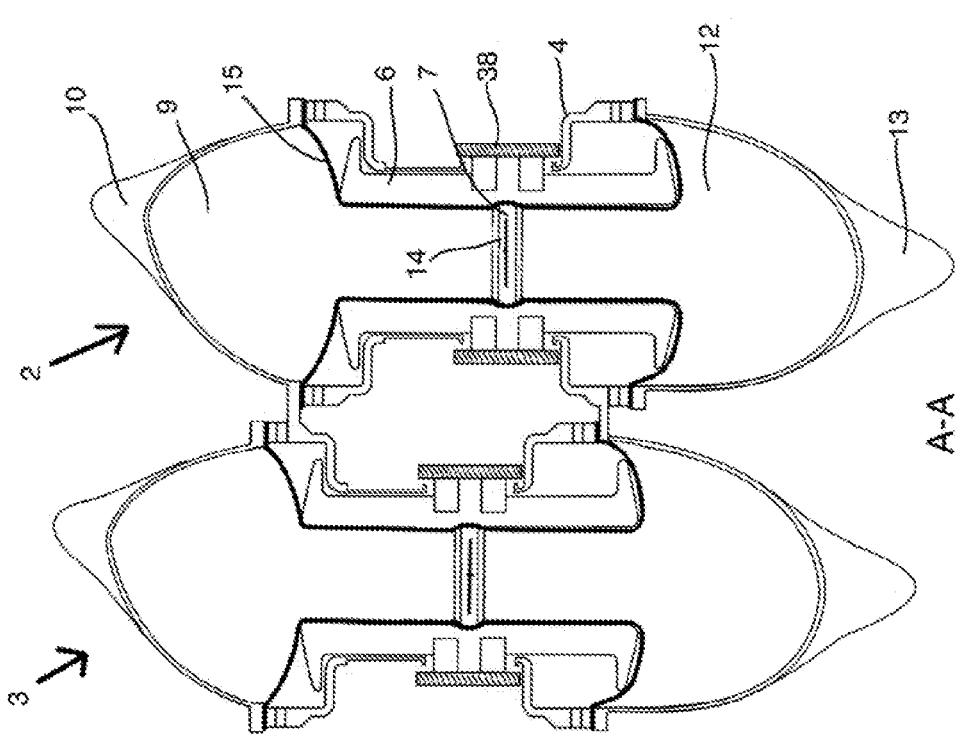

Each pump comprises an upper chamber 9 and a lower chamber 12, see FIG. 2 wherein a cross-sectional view of a four-chambered blood pumping device is shown. The upper chamber 9 has an inlet channel 10 which allows blood to enter the upper chamber 9. Said upper chamber corresponds to an atrium of the natural heart. The lower chamber 12 is provided with an outlet channel 13 which allows blood to exit the lower chamber 12. Said lower chamber 12 corresponds to a ventricle of the natural heart.

The upper and lower chambers 9, 12 are separated by a movable valve plane 7. The valve plane corresponds to the atrioventricular (AV) plane (i.e. the plane of fibrous tissue) between the atria and ventricles of a natural heart. A valve 14 is arranged in the valve plane 7, which corresponds to the tricuspid valve or the mitral valve depending on whether it is located in a pump which acts in the pulmonary circuit or in the aortic circuit.

The bottom part of the lower chamber 12 is advantageously designed to have a shape that is similar to the anatomic shape of the ventricles in the natural heart. In the four-chambered blood pumping device 1 the bottom part of the lower chamber 12 has a bag-like shape 20 designed to mimic the internal shape of the ventricle in a natural heart (see FIG. 3). The blood flow (Arrow) which passes from the upper chamber 9 through the valve 14 and into the lower chamber 12, hits a stopping surface 21 at the bottom part of the bag-like shape 20 and comes to a sudden stop, at which the flow abruptly changes direction and continues along the outlet channel 13. The turn at the inside of the bag-like portion 20 at the bottom of the lower chamber 12 forms a bend of approximately 90-340°, more preferably between 100-300°, more preferably between 105-200°, and most preferably a bend between 110-150°, which is similar to the bend inside the ventricle of a natural heart. Thereafter the blood continues into the outlet channel 13.

The cross section of the bag-like portion 20 at the bottom part of the lower chamber 12 advantageously has a triangular shape (see FIG. 3*a*) to enable an optimal flow of blood from the lower chamber 12 into the outlet channel 13. As in a natural heart, the triangular shaped cross section facilitates the formation of flow channels inside the cavity of the lower chamber 12, such that blood will arrive from different angles at the stopping surface 21 of the bag-like portion 20, stop, change direction, enter the outlet channel 13 and subsequently leave the blood pumping device through the outlet valve 19. Alternatively the cross section of the inside construction of the lower chamber 12 may have an oval (FIG. 3*b*) or circular cross section (FIG. 3*c*).

The inner walls at the bottom of the lower chamber 12, as well as the outlet channels 13 are advantageously provided with a rough surface to simulate the trabeculae carneae i.e. the muscular ridges that crisscross and project from the inner walls of the ventricles of a natural heart. Said rough surface is lined by ridges and protrusions which protrude approximately 0.01-3 mm, preferably at least 0.5-2 mm from the lower chamber 12 surface. The outlet channel 13 and bottom of the lower chamber 12 may also have smooth surfaces. The outlet channel 13 from the lower chamber 12 may also have a diameter which decreases continuously similarly to the design of the outlet of a ventricle in a natural heart (see FIG. 4).

Figure 5:
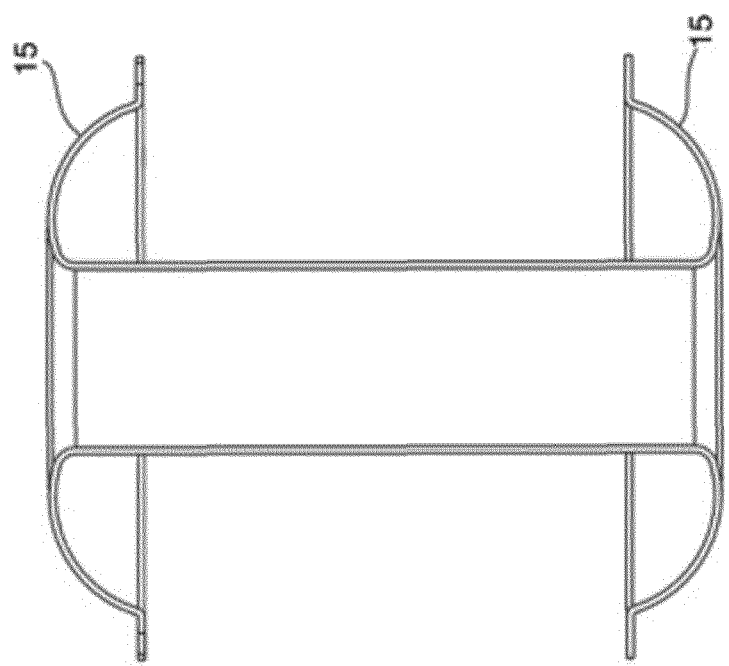
FIG. 5 is a view of the flexible lining covering the inside of the upper and lower chambers.
Figure 5:
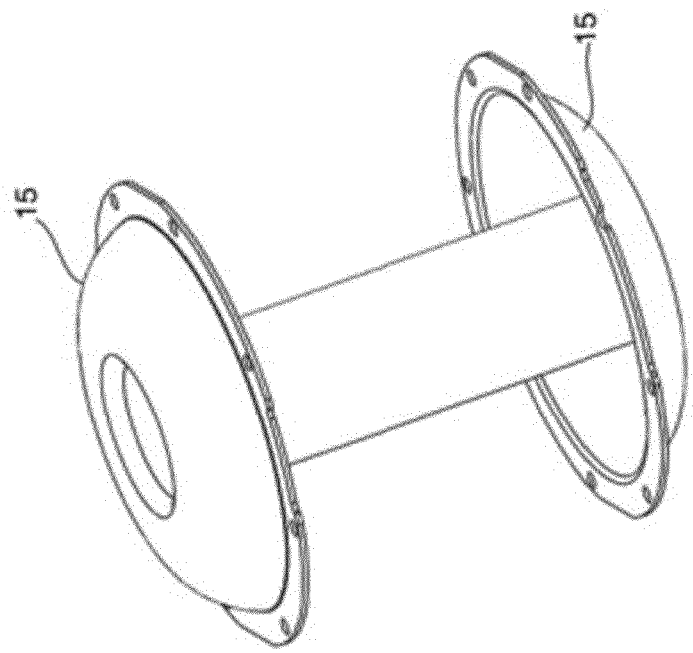

To prevent leaking of blood from the four-chambered blood pumping device 1, the insides of the upper and lower chambers 9, 12 are provided with a flexible lining 15 made from a flexible plastic or rubbery material. FIG. 5 shows the lining when removed from the chambers. The flexible lining 15 may also be comprised of two or more layers of membrane material to improve its strength. The flexible lining 15 is advantageously made from a biocompatible material like silicone, polyurethane or another biocompatible material.

Advantageously each pump 2, 3 of the four-chambered blood pumping device 1 further comprise one internal cylinder 6 provided with a valve plane 7, and one external cylinder 4, wherein the internal cylinder 6 is movably arranged inside the external cylinder 4. In this embodiment the upper and lower chambers 9, 12 which are separated by the valve plane 7 are housed inside the internal cylinder 6. The upper part of the internal cylinder 6 forms the upper chamber 9 corresponding to an atrium of the natural heart, and the lower part of the internal cylinder 6 forms the lower chamber 12 and corresponds to a ventricle of the natural heart. The valve plane 7 corresponds to the atrioventricular (AV) plane (i.e. the plane of fibrous tissue) between the atria and ventricles of a natural heart. Said valve plane 7 is provided with a valve 14 corresponding to the tricuspid valve or the mitral valve depending on whether it is located in a pump which acts in the pulmonary circuit or in the aortic circuit (see FIG. 2).

The internal cylinder 6 with the valve plane 7 is movably arranged inside the external cylinders 4, such that a pumping action is created when the internal cylinder 6 with its valve plane 7 moves linearly in the downward and upward direction inside the external cylinder 4. When the internal cylinder 6 moves in the upward direction, the valve 14 located in the valve plane 7, opens up and blood flows from the upper chamber 9 through the valve 14 and into the lower chamber 12. When the internal cylinder 6 moves in the downward direction, the valve 14 closes and the blood collected in the lower chamber 12 ejects out through the outlet channel 13. It is thus the upward and downward movements of the internal cylinder 6 with its valve plane 7 which create the pumping function of the four-chambered blood pumping device 1.

The internal and external cylinders 6, 4 are advantageously made from a stiff material, such as e.g. a biocompatible material such as, titanium, ceramics, Polytetrafluoroethylene (PTFE) coated metal, diamond coated metal or a combination thereof.

To achieve an effective and energy saving pumping function for the four-chambered blood pumping device 1 the internal cylinder 6 must move in a leak-free as well as a friction-less manner during its movement inside the external cylinder 4. Advantageously the outer wall of the internal cylinder 6 as well as the inner wall of the external cylinder 4 is provided with gliding surfaces which enables the internal cylinder 6 to move with high precision in a virtually friction- and leak-free manner (see FIG. 6 wherein the gliding surfaces are shown). The gliding surfaces are advantageously made from e.g. a ceramic material, titanium, steel, carbon fiber or any other material that will enable the internal cylinder 6 to move inside the external cylinder 4 in an essentially leek- and friction-free manner.

The fitting of the internal cylinder 6 inside the external cylinder 4 may also be made leak-free by providing the inside of the upper and lower chambers 9, 12 with a flexible lining material 15 made from a biocompatible material like silicone, polyurethane or another biocompatible material (see FIG. 5).

The orifice of the inlet channel 10 is provided with an inlet cuff 18 designed to be connected to either the systemic veins of the systemic circuit or the pulmonary veins from the pulmonary circuit. The inlet cuff 18 is preferably made from a biocompatible material such as such as plastic, rubber or metal, silicone, polyurethane, titanium, steel or any other biocompatible materials (see FIGS. 2 and 6).

The outlet channel 13 from the lower chamber 12 is advantageously provided with an outlet valve 19 as in the natural heart. The outlet valve 19 will prevent the return of blood back in to the lower chamber 12 after the blood has been ejected through the outlet channel 13. The outlet valve 19 corresponds to the aortic or pulmonary valves of the natural heart depending on whether it is located in a pump which acts in the pulmonary circuit or in the aortic circuit (see FIGS. 2 and 6).

Figure 6:
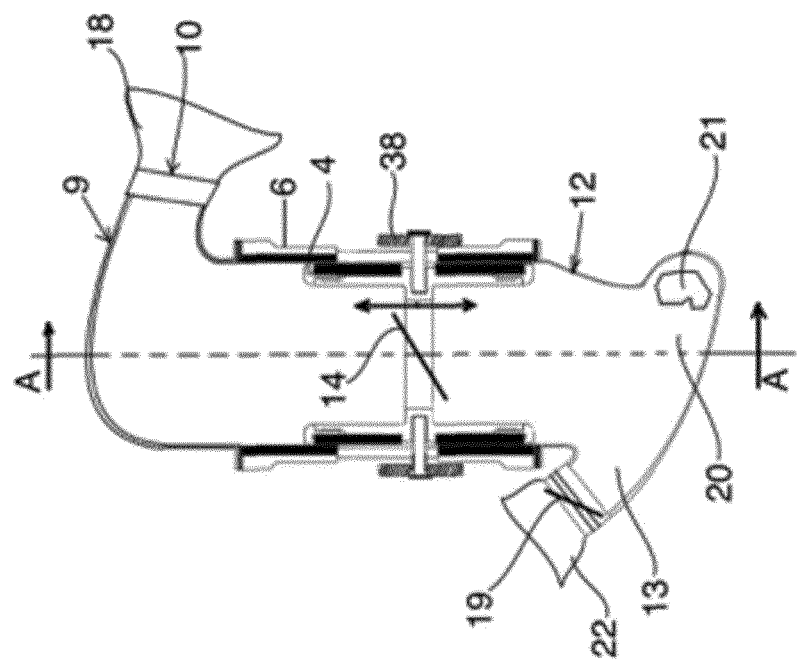
FIG. 6 shows cross sectional views of the gliding surfaces provided on the outer wall of the internal cylinder and inner wall of the external cylinder in the four-chambered blood pumping device.
Figure 6:
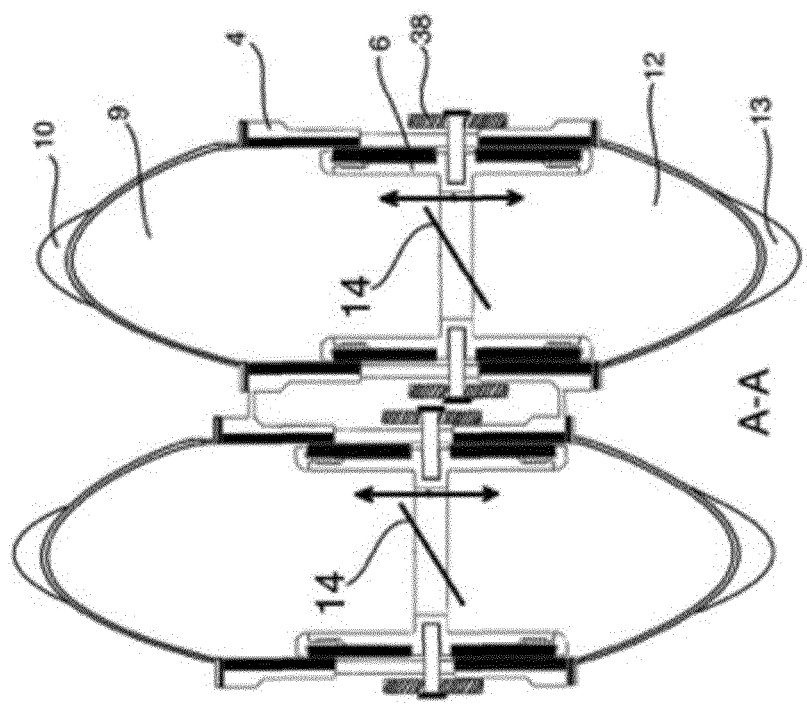

To facilitate the connection between the outlet channel 13 and the pulmonary artery of the pulmonary circuit or the aortic artery of the systemic circuit, the orifices of the outlet channels 13 are provided with outlet cuffs 22 which will serve as artery grafts (see FIGS. 2 and 6).

A pump actuating means is configured to actuate a movement of the valve plane 7 in an upward and downward direction between said upper and lower chambers 9, 12 in response to control signals from a control unit, such that when the valve plane 7 moves in an upward direction, the valve 14 provided in the valve plane 7 is in an open position allowing a flow of blood from the upper chamber 9 to the lower chamber 12, and when the valve plane 7 moves in a downward direction the valve 14 is in the closed position and blood is ejected from the lower chamber 12 through the outlet channel 13. There are many alternative ways to accomplish the pumping movement of the four-chambered blood pumping device 1, and a number of possible embodiments of how the pump actuating means achieves this linear movement of the valve plane 7 will now be described. However the skilled person will realize that the described embodiments are not the only ways to accomplish the pumping action.

Pump Actuating Means
Use of a Driving Cylinder a as Motion Generator

Figure 7:
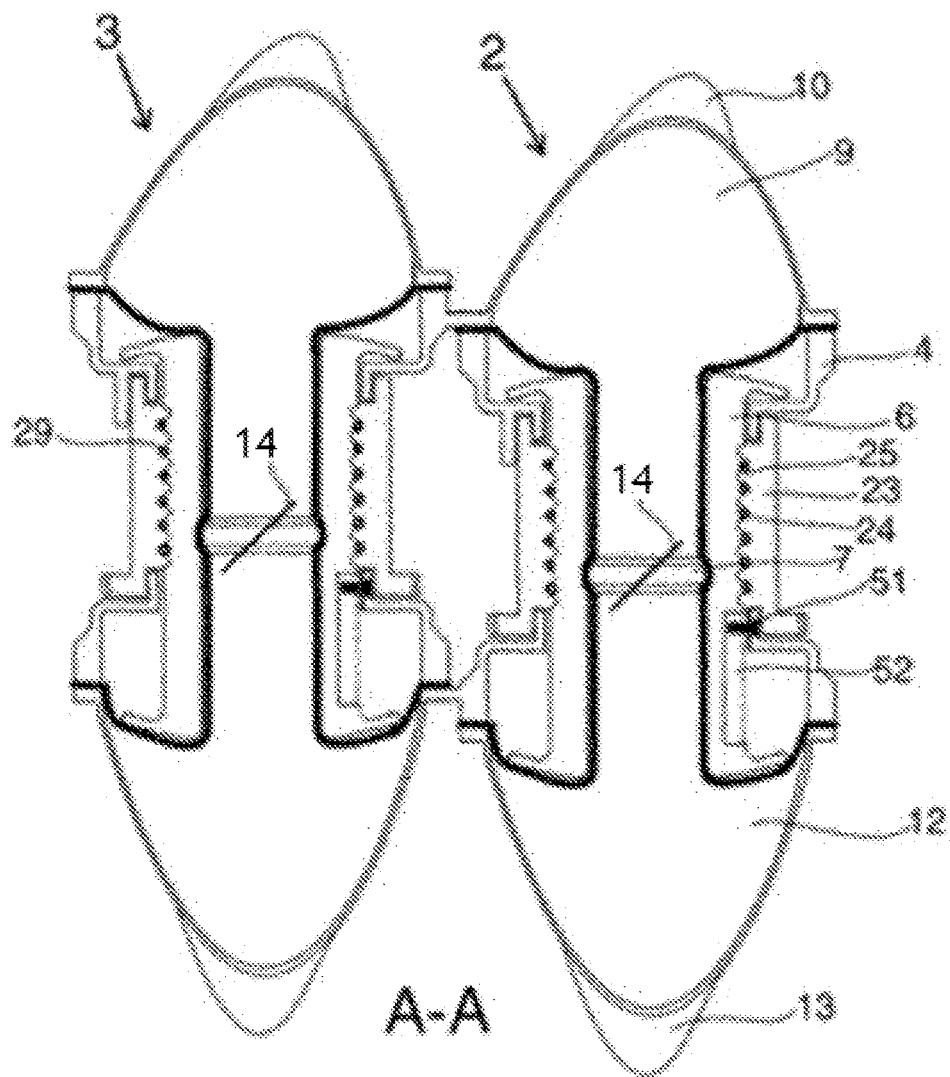
FIG. 7 shows cross sectional views of a four-chambered blood pumping device fitted with a driving cylinder as motion generator.
Figure 8:
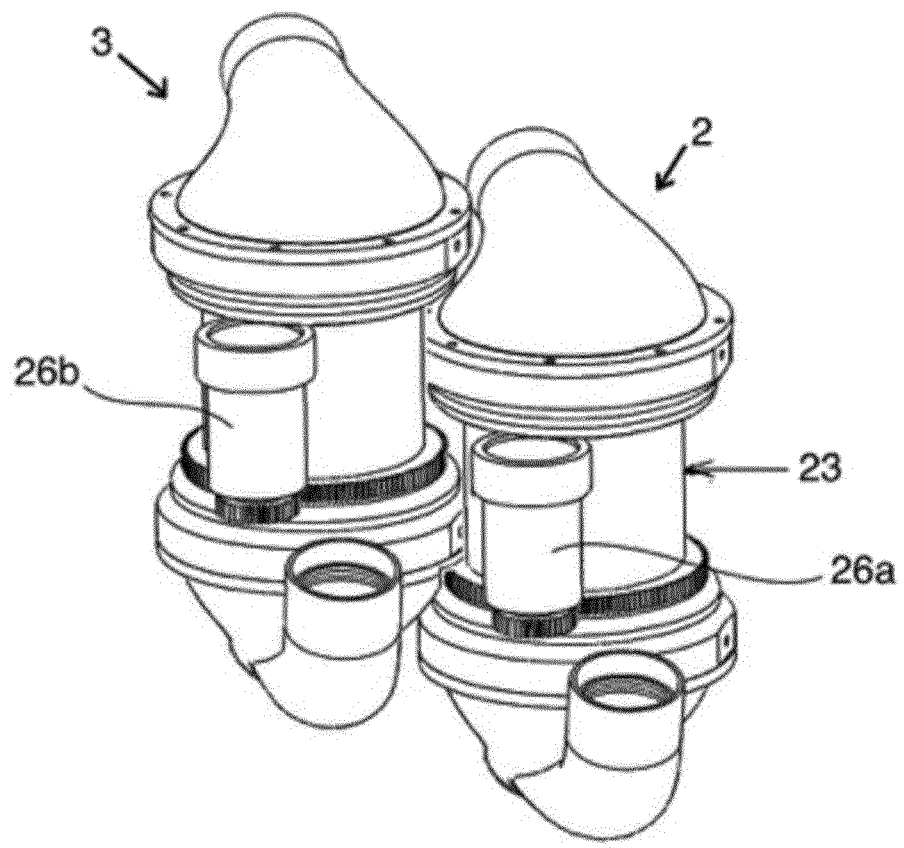
FIG. 8 is a view of a four-chambered blood pumping device fitted with a driving cylinder as motion generator.

The linear movement of the internal cylinder 6 may be accomplished by means of a driving cylinder 23 as seen in FIGS. 7 and 8 The outer surface of the internal cylinder 6 is provided with an external screw thread 24 arranged to cooperate with an internal screw thread 25 provided on the inside surface of the driving cylinder 23. Upon rotation of the driving cylinder 23 the internal cylinder 6 with it is valve plane 7 moves linearly either downwards or upwards inside the external cylinder 4 depending whether the driving cylinder 23 rotates in a clockwise or counter clockwise direction. This upward and downward movement of the internal cylinder 6 occurs by means of the cooperative arrangement between the external and internal screw threads 24, 25. Balls 29 may advantageously be arranged inside the internal screw thread 25 of the driving cylinder 23 to simulate a ball screw in which the rotation of the nut (i.e. the driving cylinder) creates the linear movement of the screw which is in this construction represented by internal cylinder 6. Advantageously the balls 29 could be replaced by rollers to create a construction like a roller screw. Both the balls 29 and rollers enhance a frictionless movement of the internal cylinder 6 inside the driving cylinder 23.

The driving cylinder 23 is advantageously operated by means of one or more electromechanical motors 26. The driving cylinder 23 is advantageously also provided with an external cogwheel 27 (see FIG. 8) on its outer surface arranged to cooperate with a motor cogwheel 28 which is connected to a rotating axle of the one or more electromechanical motors 26. When the driving cylinder 23 is operated by means of an electromechanical motor 26 the motor cogwheel 28 of the electromechanical motor 26 cooperates with the external cogwheel 27 located on the outer surface of the driving cylinder 23 and alternates the rotation of the driving cylinder 23 in either the clockwise or counter clockwise direction.

Each pump may in one alternative be operated by separate electromechanical pumps 26a and 26b (not shown). In this embodiment a first electromechanical motor 26a rotates the driving cylinder 23 of the first pump 2 in one direction e.g. the clockwise direction, which will cause the internal cylinder 6 of the first pump 2 to move in a first linear direction. In order to change the linear direction of movement for the internal cylinder 6, the electromechanical motor 26a will rotate the driving cylinder 23 in the opposite direction, i.e. the counter clockwise direction, which will cause the internal cylinder 6 to move in a second linear direction and opposite to the first linear direction. A second electromechanical motor 26b operates the second pump 3 in a similar fashion. The first and second electromechanical motors 26a 26b are coupled to each other electrically and are synchronized to each other to move both pumps 2, 3 simultaneously in the same direction and at the same velocity.

Alternatively one single electromechanical motor 26 operates both the first and second pumps 2 and 3 together. This means that the single electromechanical motor 26 rotates the first and second driving cylinders 23a 23b for both the first and second pumps 2, 3 in a first direction, e.g. the clockwise direction which will cause the first and second internal cylinders 6a and 6b to move in a first linear direction. Thereafter the same electromechanical motor 26 rotates the first and second driving cylinders 23a 23b for both the first and second pumps 2, 3 in the opposite direction e.g. the counter clockwise direction which will cause the first and second internal cylinders 6a, 6b to move in a second linear direction and opposite to the first linear direction. This means that one single electromechanical motor 26 will alternate between the clockwise and counter clockwise directions to enable the up and down movement of the internal cylinders 6a, 6b.

Figure 4:
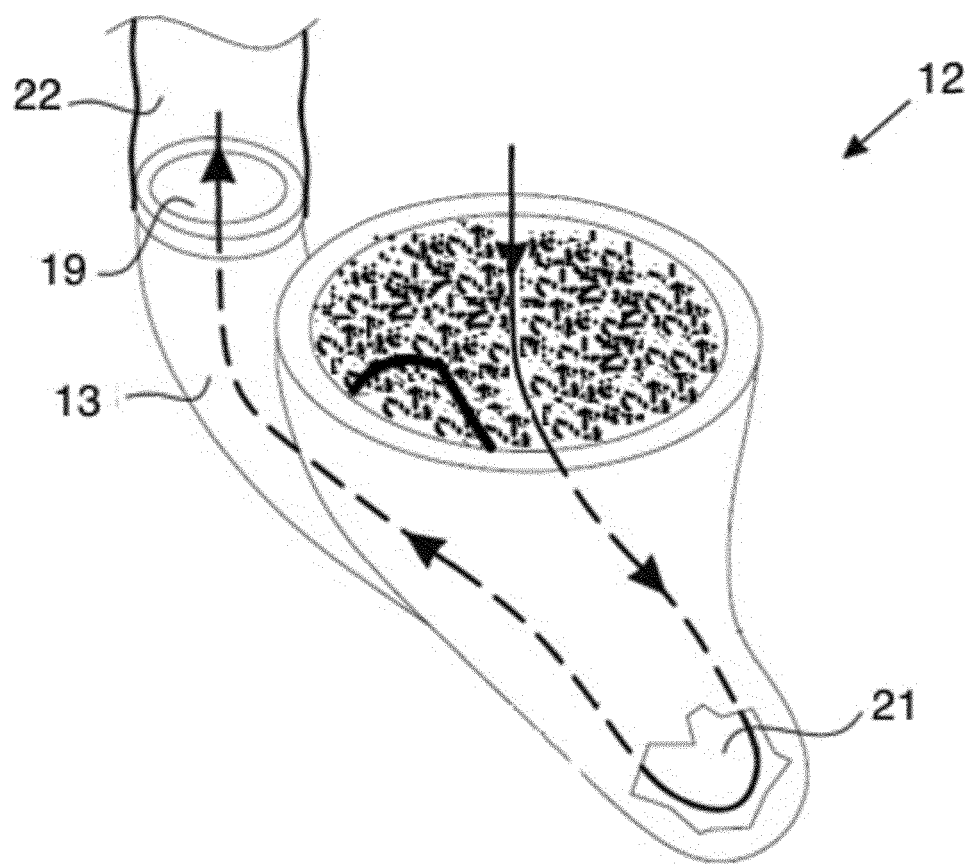
FIG. 4 is a detailed view of the rough surface on the inside of the lower chamber.

Alternatively two electromechanical motors 26a, 26b, operate both pumps 2, 3 wherein each one of the electrical motors 26a, 26b operates the internal cylinders 6a, 6b of both pumps 2, 3 only in one direction (see FIGS. 4 and 5). A first electromechanical motor 26a rotates the driving cylinders 23a, 23b of both pumps 2, 3 in a first direction, e.g. in the clockwise direction, which will cause the internal cylinders 6a, 6b of both pumps 2, 3 to move in a first linear direction. A second electrical motor 26b rotates the driving cylinders 23a, 23b of both pumps 2, 3 in the opposite direction, e.g. the counter clockwise direction, which will cause the internal cylinders 6a, 6b of both pumps 2, 3 to move in a second linear direction, and opposite to the first linear direction. In this embodiment the two electromechanical motors 26a, b will alternate their operations, i.e. when the first electromechanical motor 26 a operates the second electromechanical motor 26 b rests, and vice versa.

Further there is at least one internal cylinder rotation-preventing member which prevents the internal cylinder 6 to be rotated by the action of the driving cylinder 23 to allow only the upward and downward movement of the internal cylinder 6. The internal cylinder rotation-preventing member may be represented by at least one rod 51 connected to the external cylinder to be extended inside a longitudinal recessed groove 52 in the wall of the internal cylinder.

Use of a Stator Cylinder 34 as Pump Actuating Means

Figure 9:
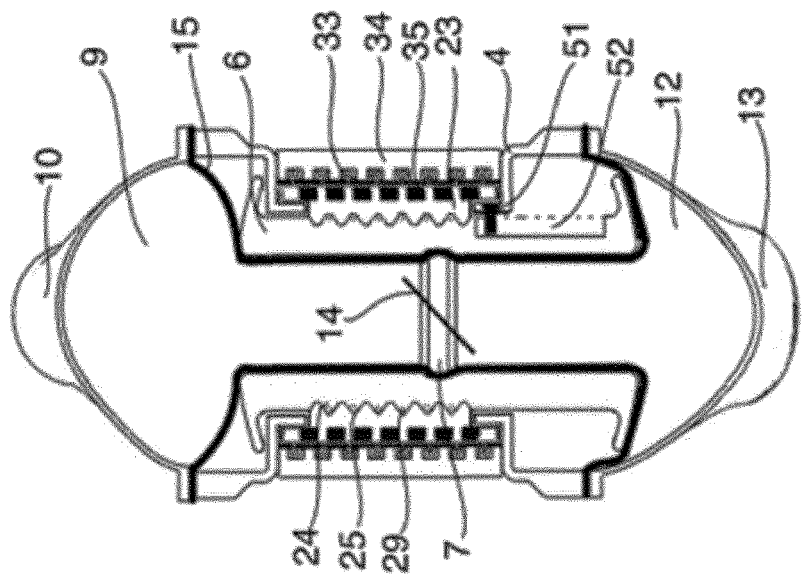
FIG. 9 shows cross sectional views of a four-chambered blood pumping device fitted with a cylinder provided with an integrated stator coil.
Figure 9:
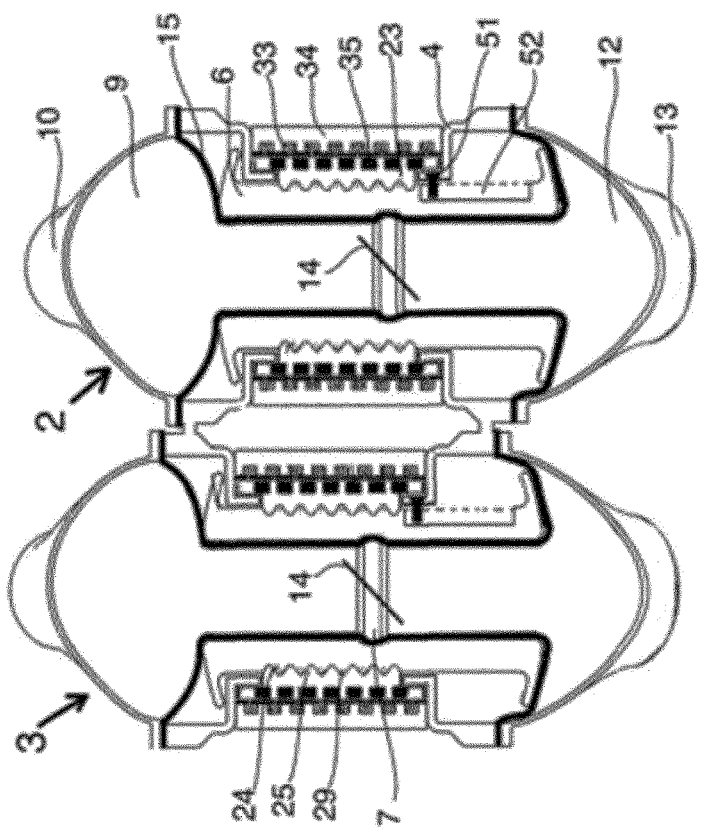
Figure 10:
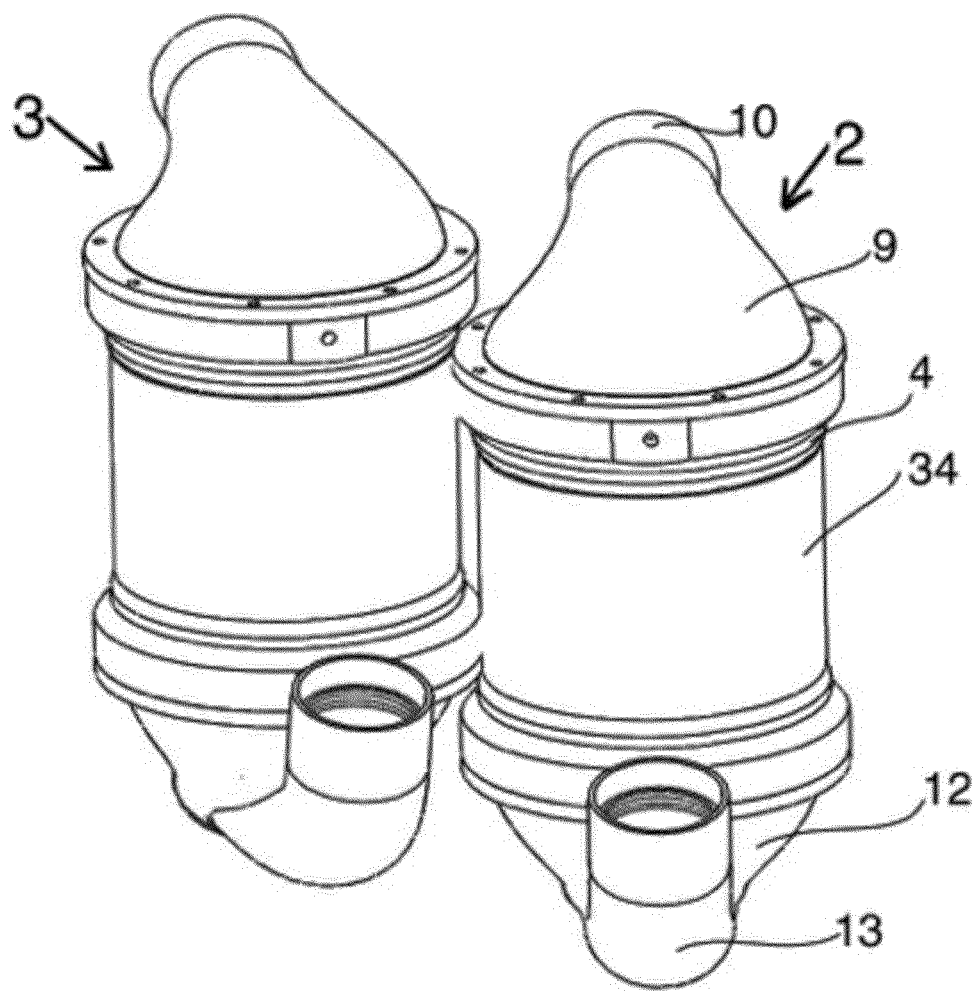
FIG. 10 is a view of a four-chambered blood pumping device fitted with a cylinder provided with an integrated stator coil.

The upward and downward movements of the internal cylinder 6, i.e. the pumping function may also be accomplished by means of a cylinder with an integrated stator coil 33 (see FIG. 9 and FIG. 10). The stator coil 33 is fixed to a stator cylinder 34 which is connected to the external cylinder 4 to prevent any possibility for the stator cylinder to rotate. One or more permanent magnets 35 are embedded and integrated with the outer surface of the driving cylinder 23 to enable the internal cylinder 6 to rotate when an electrical current is applied through the stator coil 33. In this embodiment the entire driving cylinder 23 functions as a rotor in an electromechanical motor 26 and thus the stator cylinder 34 together with the driving cylinder 23 works as an electromechanical motor 26. An external screw thread 24 is provided on the outer surface of the internal cylinder 6 which enables the internal cylinder 6 to be rotated into an internal screw thread 25 provided on the inside surface of the driving cylinder 23.

Upon rotation of the driving cylinder 23 the internal cylinder 6 with it is valve plane 7 moves linearly either downwards or upwards inside the external cylinder 4 depending whether the driving cylinder 23 rotates in a clockwise or counter clockwise direction. This upward and downward movement of the internal cylinder 6 occurs by means of the cooperative arrangement between the external and internal screw threads 24, 25. Balls 29 may advantageously be arranged inside the internal screw thread 36 of the driving cylinder 23 to create a construction like a ball screw in which the rotation of the nut (driving cylinder 23) creates the linear movement of the screw which is in this construction represented by internal cylinder 6. Advantageously the balls 29 could be replaced by rollers to create a construction like a roller screw. Both the balls 29 or rollers enhance a frictionless movement of the internal cylinder 6 inside the driving cylinder 23.

The up- and down movement is accomplished by the action of the magnetic field which is created between the stator cylinder 34 and the permanent magnets 35 on the surface of the driving cylinder 23. Thus the linear movement of the internal cylinder 6 is created by the rotation of the driving cylinder 23 realized by the cooperative engagement between the external screw thread 24 on the outer wall of the internal cylinder 6 and the internal screw thread 36 provided on the internal surface of the driving cylinder 23.

Cylinder Actuating Assembly

The pump actuating means may in another advantageous embodiment comprise a cylinder actuating assembly 37 (see FIG. 11) which is connected to the internal cylinder and is powered by means of a motion generator.

Figure 11:
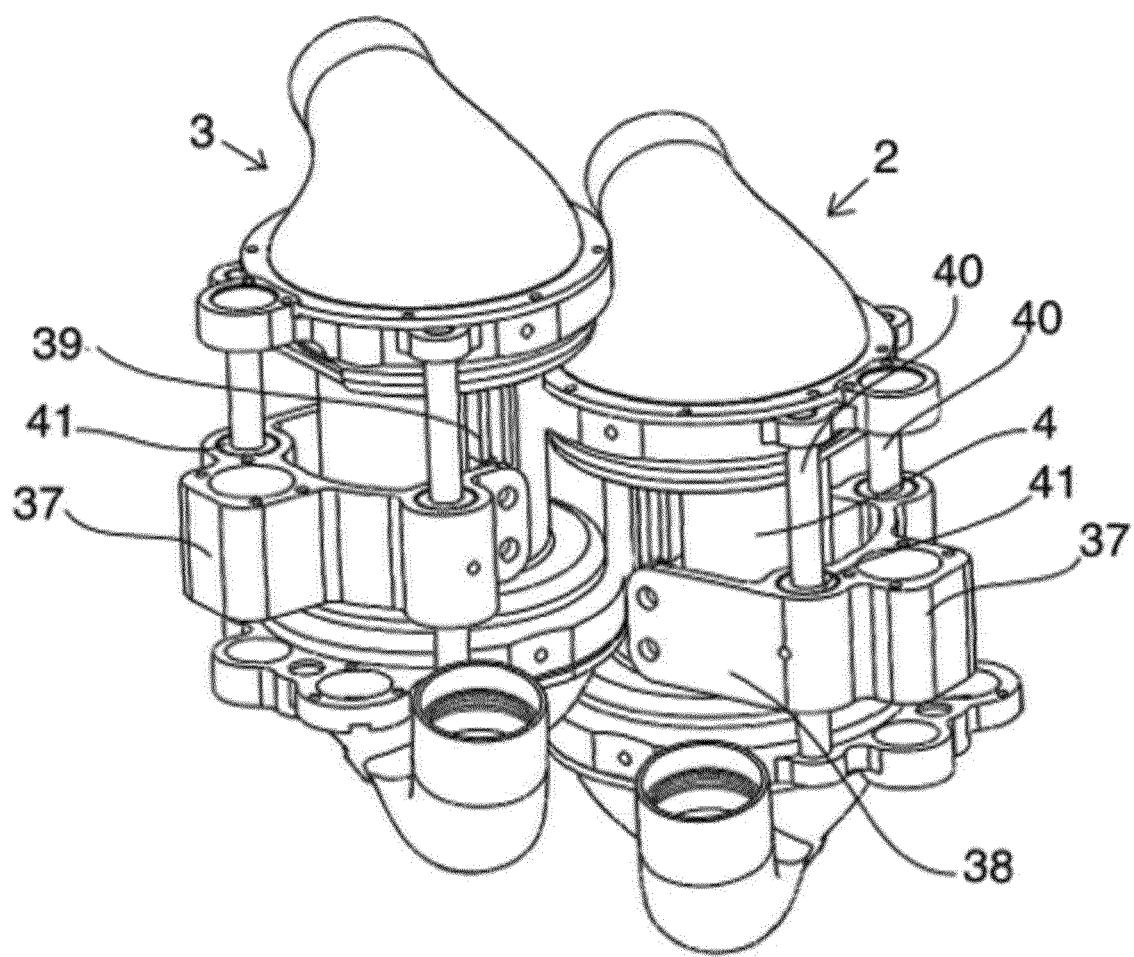
FIG. 11 is a view of a four-chambered blood pumping device fitted with a cylinder actuating assembly.

FIG. 11 shows a four-chambered blood pumping device 1 wherein the pumps 2, 3 are provided with cylinder actuating assemblies 37. In this embodiment the cylinder actuating assembly 37 is a device which has connector arms 38 which extend around at least half of the circumference of the external cylinder 4. The external cylinder 4 is provided with rectangular openings 39 on each side of the internal cylinder 6 through which the ends of the connector arms 38 are directly fixed to the internal cylinder 6. The shape and size of the rectangular openings 39 on each side of the external cylinder are accommodated to enable the cylinder actuating assembly 37 to move the internal cylinder 6 linearly up and down inside the external cylinder 4.

The cylinder actuating assembly 37 further comprises at least two stabilizing members 40, which in an advantageous embodiment are rods which extend and run through a bearing support 41 located in each connector arm 38 of the cylinder actuating assembly 37. Said stabilizing members 40 run in parallel to the direction of movement of the internal cylinder 6. The stabilizing members 40 stabilize the linear up-and-down movement of the cylinder actuating assembly 37 and enable it to move along the outer wall of the external cylinder 4 with high precision. Both the stabilizing members 40 and the inside of the bearing support 41 are advantageously made from a friction-less material such as ceramics to enable a friction-less up-and-down movement of the pump-actuating member.

The cylinder actuating assembly 37 is powered by a motion generator to enable the movement of the internal cylinder 6 in an up-and-down movement inside the external cylinder 4.

Use of a Ball or Roller Screw as Motion Generator

In one advantageous embodiment the motion generator may be a ball or roller screw 42 or similar device In the ball or roller screw 42 motion generator the ball screw or roller screw act as a linear actuator that translates a rotational motion created by power source, such as e.g. an electromechanical motor 26 into linear motion with little friction (see FIGS. 1 and 2). In this embodiment the nut 43 of the ball or roller screw 42 is integrated with the cylinder actuating assembly 37 (described above), which together with its connector arms 38, extends around the external cylinder 4 and connects directly to the internal cylinder 6 through the rectangular openings 39 on each side of the external cylinder 4.

The screw 44 of the ball or roller screw 42 is advantageously provided with a cogwheel 45 in a cooperative arrangement with a motor cogwheel 28 of an electromechanical motor 26. When the electromechanical motor 26 rotates the motor cogwheel 28, said motor cogwheel 28 cooperates with the cogwheel 45 on the screw 44 of the ball or roller screw and rotates said screw 44. When the screw 44 rotates, its rotational movement is translated into a linear movement of the cylinder actuating assembly 37 i.e. the nut 43 with the connector arms 38 which moves in an upward direction or a downward direction depending on the direction of rotation of the electromechanical motor 26.

When the electromechanical motor 26 rotates the screw 44 of the ball or roller screw 42 in a first direction, the cylinder actuating assembly 37 (and the internal cylinder 6) moves in a first linear direction along the screw 44 of the ball or roller screw 42. When the electromechanical motor 26 rotates the screw 44 of the ball or roller screw 42 in a second direction, the cylinder actuating assembly 37 (and the internal cylinder 6) moves in a second linear direction along the screw 44 of the ball or roller screw 42. Said second direction is opposite to the first direction. The electromechanical motor 26 alternates its rotation between the first and the second rotation, thereby enabling the up-and-down pumping motion of the internal cylinder 6. Each pump contains a cylinder actuating assembly 37 with motion generator and both pumps 2, 3 operate simultaneously and in the same direction.

Use of a Hydraulic or Pneumatic Pumping System as Motion Generator

Figure 12:
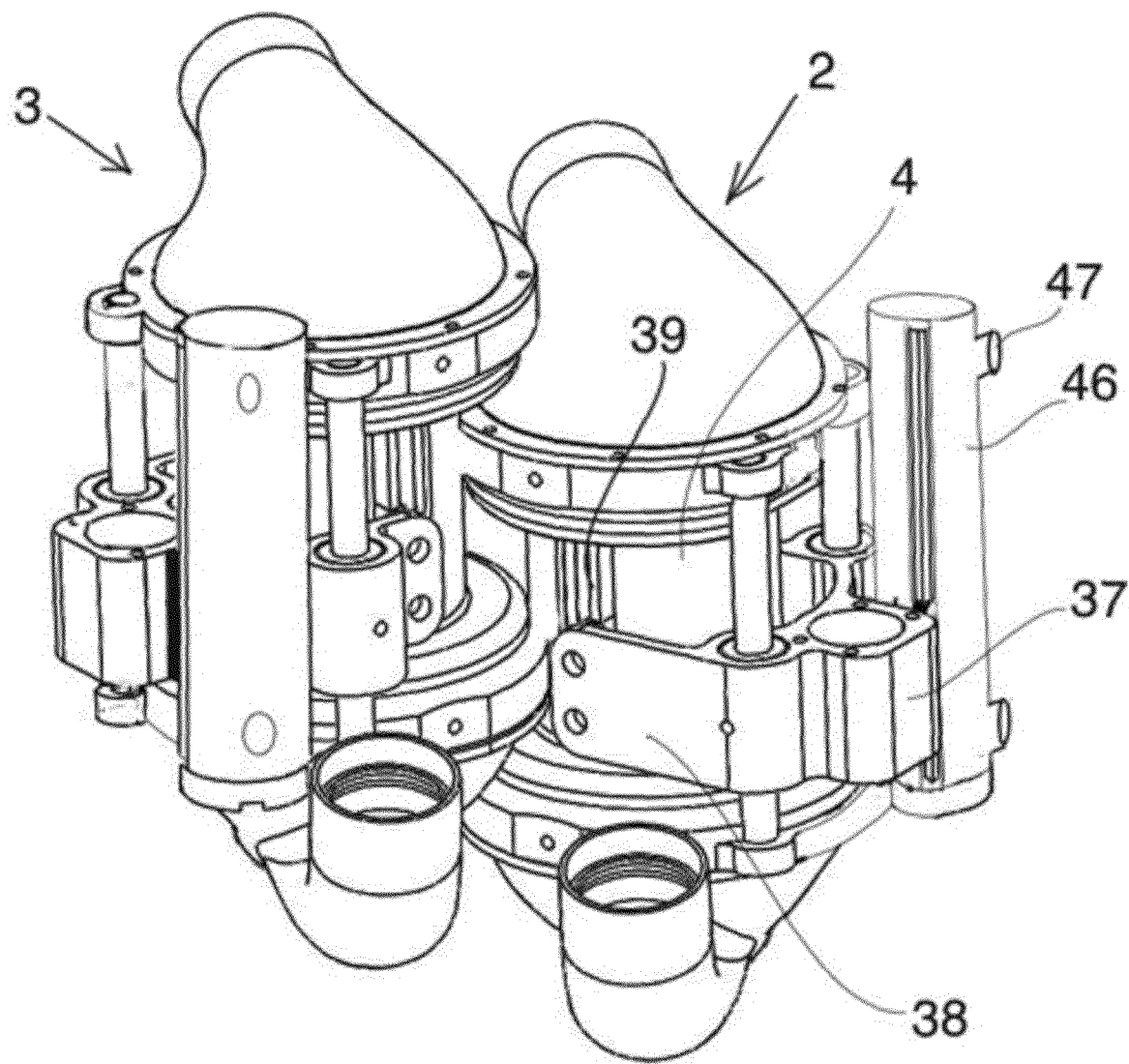
FIG. 12 is a view of a four-chambered blood pumping device fitted with a hydraulic or pneumatic pumping system.

In an alternative embodiment the motion generator may be a hydraulic or pneumatic pumping system which when connected to an internal cylinder 6 by means of a cylinder actuating assembly 37 (as described herein) enables the up-and-down movement of the internal cylinder 6 inside the external cylinder 4 (see FIG. 12). In this embodiment the upward and downward linear movements of the internal cylinder 6 are created by the pushing and pulling action of a hydraulic or pneumatic cylinder 46 (see FIGS. 12, and 2). The cylinder rods (not shown) of the hydraulic or pneumatic pumping cylinders 46 are directly connected to the cylinder actuating assembly 37 and the two connector arms 38 of the cylinder actuating assembly 37 extend around at least part of the circumference of the external cylinder 4 to connect to opposite sides of the internal cylinder 6 through rectangular shaped openings 39 in the wall of the external cylinder 4. When the hydraulic or pneumatic cylinder 46 operates, i.e. when the piston rod inside the hydraulic or pneumatic cylinder 46 moves in and out, the cylinder actuating assembly 37 moves simultaneously with the piston rod and thereby enables the up-and-down movement of the internal cylinder 6 inside the external cylinder 4.

The hydraulic cylinder 46 is operated by a hydraulic pump (not shown) provided e.g. inside the abdomen of the subject, or alternatively outside the subject. A hydraulic tube (not shown) connects the hydraulic pump to the hydraulic cylinder 46 via two connections nipples 47 provided on the hydraulic cylinder 46 to transport the hydraulic oil between the hydraulic pump and hydraulic cylinder 46. The two hydraulic cylinders 46 may operate by means of only one hydraulic pump which means that they are synchronized to each other and move together in the same direction and at the same velocity, or alternatively by two hydraulic pumps. The pneumatic cylinder is powered by compressed gas supplied by an external source.

Each pump 2, 3 of the blood pumping device contain a cylinder actuating assembly powered by means of a hydraulic or pneumatic pumping system as motion generator. Both pumps of the heart operate simultaneously and in the same direction.

Pumping Action of the Four-Chambered Heart

Figure 13:
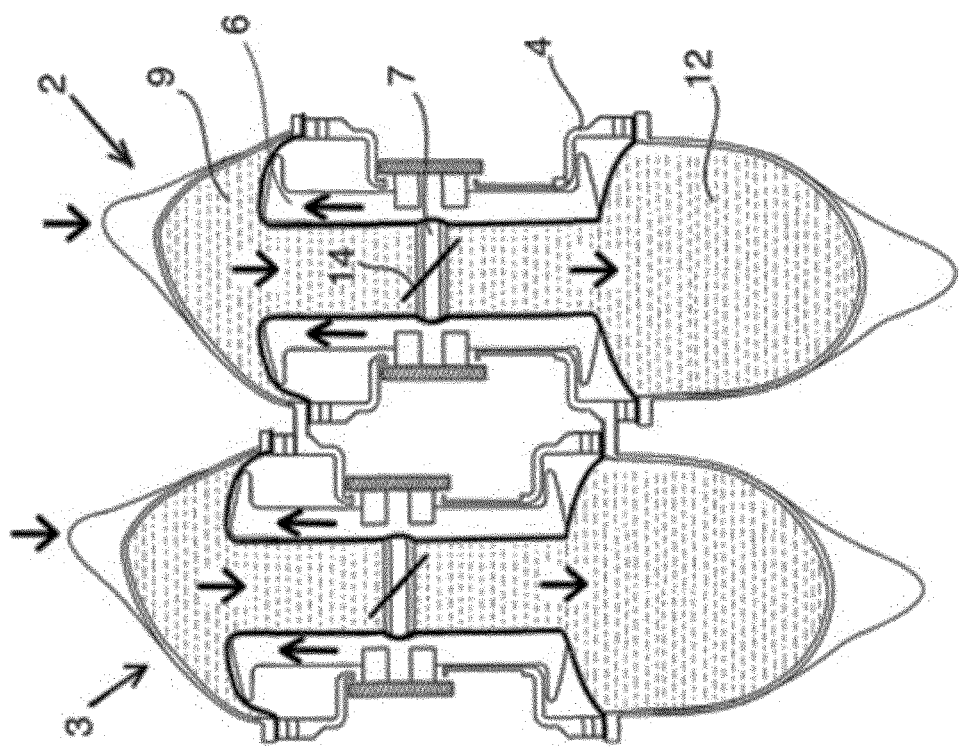
FIG. 13 is a cross sectional view of the four-chambered blood pumping device showing how the internal cylinders move upwards and blood flows from the upper chambers through the open valves and into the lower chambers.
Figure 14:
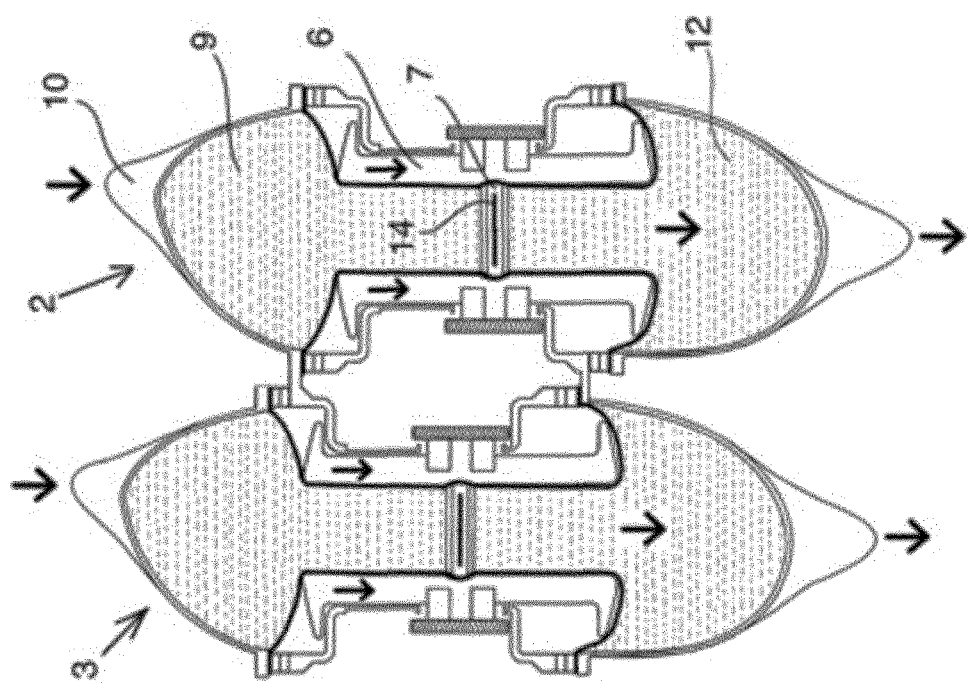
FIG. 14 is a cross sectional view of the four-chambered blood pumping device showing how the internal cylinders move downwards ejecting blood from the lower chambers through the outlet channels.

The pumping action of the four-chambered heart will now be described. The first and second pumps 2, 3 are identical and therefore the pumping function now described applies to both pumps (see FIGS. 13 and 14).

Blood enters the upper chamber 9 of the four-chambered blood pumping device 1 through the inlet channel 10. In one pump motion cycle deoxygenated blood arrives from the systemic circuit to enter the first pump 3, and oxygenated blood arrives from the pulmonary circuit to enter the second pump 2. When the upper chamber 9 has been filled with blood, the valve 14 located in the valve plane 7 of the internal cylinder 6 switches to an open position when the internal cylinder 6 moves upwards in a first linear direction inside the external cylinder 4 (see FIG. 13). When the internal cylinder 6 moves upwards, blood collected in the upper chamber 9 flows through the open valve 14 located in the valve plane 7 and into the lower chamber 12. The linear movement of the internal cylinder 6 may be realized as described elsewhere in this document.

Figure 3:
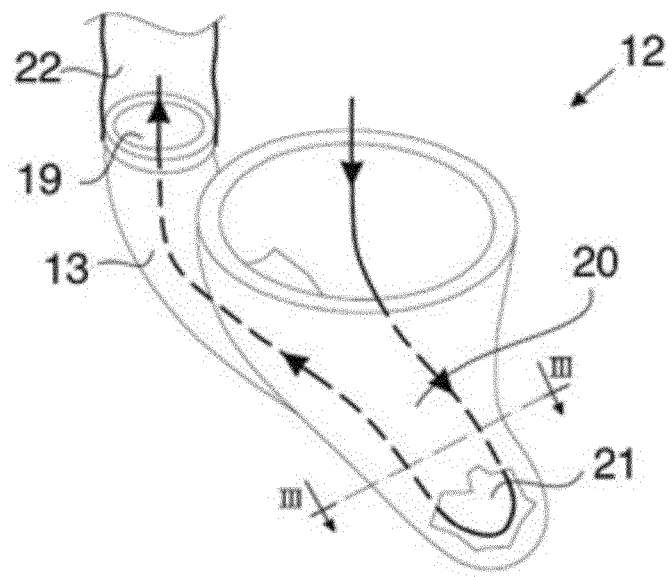
FIG. 3 shows the blood flow past the bag-like portion area of the lower chamber to the outlet channel.
Figure 3:
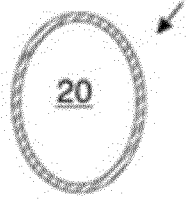
Figure 3:
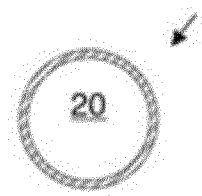
Figure 3:
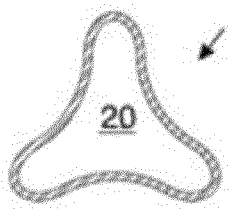

After the lower chamber 12 has filled with blood, the valve 14 located in the valve plane 7 closes. The internal cylinder 6 now moves downwards and in a second linear direction inside the external cylinder 4 and pushes the blood towards the bottom part of the lower chamber 12, (see FIG. 14). When the blood is pushed towards the bottom of the lower chamber 12 it enters the bag-like portion 20 and hits the stopping surface 21, stops, changes direction and exits the lower chamber 12 through the outlet channel 13. The outlet valve 19 located at the orifice of the outlet channel opens during the outflow of blood, and thereafter closes to prevent blood from re-entering the lower chamber 12 through the outlet channel 13 (FIG. 3).

Use of the Four Chambered Blood Pumping Device as a Total Artificial Heart Implant The four-chambered blood pumping device 1 may be used as a Total Artificial Heart (TAH) Implant replacing a natural heart in a subject.

In order to implant the blood pumping device inside a subject the surgeon removes diseased heart but keeps some parts of the right and left atrium walls including the exits of veins feeding blood into the atria of a natural heart. The remaining parts of the atria are sutured to the inlet cuff 18 of the four-chambered blood pumping device 1. A first end of said inlet cuff 18 is advantageously made from a wide strip of vessels graft tissue which surrounds the inlet channel 10 of the upper chamber 9 which is sutured to the remaining wall parts of the atria. The second end of the inlet cuff 18 is advantageously fitted with a fast connection such as a blocking stripe made from glass fiber reinforced silicone or other material used for this purpose or other fast connection can be used. Said fast connection connects to the inlet channel 10 of the four-chambered blood pumping device 1. Alternatively, the collar cuff 18 may be glued to the inlet channel 10 of the four-chambered blood pumping device 1.

The outlet channels 13 of the four-chambered blood pumping device 1 are connected to the aortic and pulmonary arteries by means of suturing to a an outlet cuff 22 which also advantageously is made from a vessel graft material. Advantageously also the outlet cuff 22 fitted with a fast connection such as a blocking stripe made from glass fiber reinforced silicone or other material used for this purpose, or other fast connection can be used. Said fast connection connects to the outlet channel 13 of the four-chambered blood pumping device 1. Alternatively, the outlet cuff 22 may be glued to the outlet channel 13 of the four-chambered blood pumping device 1.

The energy to power the pump actuating means may be supplied by an external source via a cable through the skin, or alternatively by an implanted battery. The implanted battery may be recharged from the outside via a cable or by means of induction or ultra sound.

The energy to power the pump actuating means is supplied by an implantable rechargeable battery (not shown) or by an external energy source such as e.g. rechargeable batteries placed around the waist or included in a jacket worn by the subject. The external energy source gives the required power directly to the pump actuating means and to the implanted battery to be recharged via a cable or by means of induction or ultra sound. If for some reason the subject for a short period removes the external energy source, e.g. to take a shower, the internal battery will supply the pump actuating means with enough energy for a short period of time.

The pump actuating means is advantageously controlled by an implanted micro-computer or electronic chips. The input information to the computer is advantageously provided from the sinus node (which remains inside the body after removing the diseased heart), via pacemaker-type electrodes. However, the micro-computer or electronic chips may also receive signals from pressure sensors placed around major arteries. When the patient changes his physical activities the blood pressure will reflect the situation. The micro-computer or the electronic chips will send information to the pump actuating means to change its pumping activity accordingly. If for some reason the micro-computer or electronic chips are not receiving any input information, the pump actuating means will continue at a constant level of activity, and instead the patient will have to adjust his physical activities. The body temperature, which increases with physical activity, may also be used to activate the pump actuating means during high physical efforts.

Test of a Four-Chambered Blood Pumping Device in a Pig Trial 1

In a first trial a four-chambered blood pumping device comprising two identical pumps was connected to a pig without removal of the natural heart. A pig weighing about 50 kilograms was anesthetized and laid on its back. A pulse oximeter for measuring the saturation of oxygen in blood was connected to the tail. The chest was opened and the heart was exposed. A cardiopulmonary bypass device (heart-lung machine) was connected to the pig and took over the function of the heart and lungs. Four vessel grafts were sewn to the heart and larger vessels of the heart; a first graft was sewn to the left atrium, a second to the aorta leaving the left ventricle, a third to the right atrium and a fourth to the pulmonary artery leaving the right ventricle. All vessel grafts were filled with blood and saline solution and were closed at the free ends with hemostatic forceps.

The blood pumping device was thereafter connected to the body by means of the four vessel grafts. The left atrium vessel graft was connected to the inlet channel of the upper chamber in a first) pump. The right atrium vessel graft was connected to the inlet channel of the upper chamber in the second pump. The aorta vessel graft was connected to the outlet channel of the lower chamber in the first pump and the pulmonary artery vessel graft was connected to the outlet channel of the lower chamber in the second pump. All vessel grafts were connected to the four-chambered blood pumping device by means of cable ties.

After connecting the blood pumping device to the heart of the pig, blood was let through the device. Venting of the pumping device was accomplished by means of placing cannulas in each of the outlet channel vessel grafts from the lower chambers while moving the valve plane manually between the upper and lower chambers. Complete venting took about 10-15 min and thereafter a computer was connected to the blood pumping device to control the device.

After venting of the four-chambered blood pumping device was accomplished the cardio pulmonary device was turned off and the heart was compressed by applying a clamp to stop the function of the natural heart. The four-chambered blood pumping device was started and allowed to pump with 100 beats per minute with a systolic phase length of 200 milliseconds (ms) and diastolic phase length of 400 ms (i.e. a total time of 600 ms/beat). Blood pressure, oxygen saturation and the pressure in the central venous system was registered. The computer registered power consumption during the systole and diastole for each beat.

Oxygen rich blood entered the upper chamber of the first pump (i.e. the pump acting in the systemic circuit) from the left atrium of the pig's natural heart. The oxygenated blood continued through the open valve and into the lower chamber when the valve plane moved in the upward direction towards the upper chamber. Blood was thereafter ejected from the lower chamber through the outlet channel and into the aorta as the valve plane (with the valve closed) moved in opposite direction towards the lower chamber. Deoxygenated blood entered the upper chamber of the second pump (i.e. the pump acting in the pulmonary circuit) from the right atrium of the pig's natural heart. The deoxygenated blood continued through the open valve and into the lower chamber when the valve plane moved in the upward direction towards the upper chamber. Blood was thereafter ejected from the lower chamber through the outlet channel and into the pulmonary artery and lungs as the valve plane (with the valve closed) moved in opposite direction towards the lower chamber.

The four-chambered blood pumping device gave a pulsating blood flow through the circulatory system much like the flow from a natural heart. The pig had good oxygen saturation indicating sufficient blood flow through the lungs. Pumping continued for 16-17 minutes before stopping. The blood pumping device was disconnected and the pig was put to sleep while still under anesthesia.

Trial 2

In a second trial the procedure as disclosed in example 1 was repeated except that after about 1 minute the pumping frequency was lowered to 85 beats per minute with a systolic phase length of 200 ms and diastolic phase length of 500 ms. The four-chambered blood pumping device was stopped after about 17 minutes Results The four-chambered blood pumping device delivered a pumping flow and pressure similar to that of a natural heart. The animal was doing generally well after the cardiopulmonary bypass device was disconnected and the four-chambered blood pumping device was turned on. The oxygen saturation was optimal throughout the running time and in fact metabolic acidosis formed during the time spent on the cardiopulmonary bypass device disappeared when the four chambered blood pumping device was started. The results from the two trials can be seen in tables 1 and 2 below.

TABLE 1

Results from trial 1

| Time after start (min) | No. of beats/min | Systolic time (ms) | Diastolic time (ms) | Time/beat (ms) | Stroke length (mm) | Current (A) | Blood pressure (mmHg) | Central venous pressure (mmHg) |
|---|---|---|---|---|---|---|---|---|
| 1 | | | | | | | 41/26 | 19 |
| 2 | | | | | | | 51/23 | 17 |
| 3 | 100 | 200 | 400 | 600 | 18.5 | 5.75 | | |
| 5 | 100 | 200 | 400 | 600 | 17.5 | 6 | | |
| 8 | 100 | 200 | 400 | 600 | 18.0 | 6 | 48/28 | 20 |
| 12 | 100 | 200 | 400 | 600 | 18.0 | 6 | | |
| 15 | 100 | 200 | 400 | 600 | 17.5 | 6 | | |
| Mean | 100 | 200 | 400 | 600 | 17.9 | 5.95 | 47/26 | 18.6 |

TABLE 2

Results from trial 2

| Time after start (min) | No. of beats/min | Systolic time (ms) | Diastolic time (ms) | Time/beat (ms) | Stroke length (mm) | Current (A) | Blood pressure (mmHg) | Central venous pressure (mmHg) | $O_2$-satur. (%) |
|---|---|---|---|---|---|---|---|---|---|
| 1 | 100 | 200 | 400 | 600 | 17.5 | 6.65 | | | |
| 2 | 85 | 200 | 500 | 700 | 17.5 | 5.65 | | | |

TABLE 2-continued

Results from trial 2

| Time after start (min) | No. of beats/min | Systolic time (ms) | Diastolic time (ms) | Time/beat (ms) | Stroke length (mm) | Current (A) | Blood pressure (mmHg) | Central venous pressure (mmHg) | $O_2$-satur. (%) |
|---|---|---|---|---|---|---|---|---|---|
| 3 | | | | | | | 38/21 | 19 | 98 |
| 5 | 85 | 200 | 500 | 700 | 17.5 | 5.6 | | | |
| 7 | | | | | | | 62/39 | 22 | 97 |
| 10 | 85 | 200 | 500 | 700 | 17.5 | 6.25 | 50/30 | 23 | 99 |
| Mean* | 85 | 200 | 500 | 700 | 17.5 | 6.03 | | | |
| Mean | 88.75 | 200 | 475 | 675 | 17.5 | 5.83 | 50/30 | 21.3 | 98 |

*mean values of 85 beats/min only

The average current consumption was 5.95 ampere (A) when the pump delivered 100 beats/min. When the four-chambered blood pumping device was loaded with blood the length of each stroke (i.e. the distance moved by the valve plane between the upper and lower chambers) was 17.9 mm. The average current consumption was lowered to 5.83 A when the pump delivered 85 beats/minute and the length of each stroke was then 17.5 mm. With a frequency of 100 beats per minute a systolic pressure of 46 mmHg and diastolic pressure of 26 mmHg was achieved. When the frequency was lowered to 85 beats per minute a pressure of 50/30 mmHg was achieved. The blood pumping device produced an average central venous pressure of 18.6 mmHg at 100 beats per minute and 21.3 mmHg at 85 beats per minute.

Blood Pumping Device with Two Chambers

Figure 15:
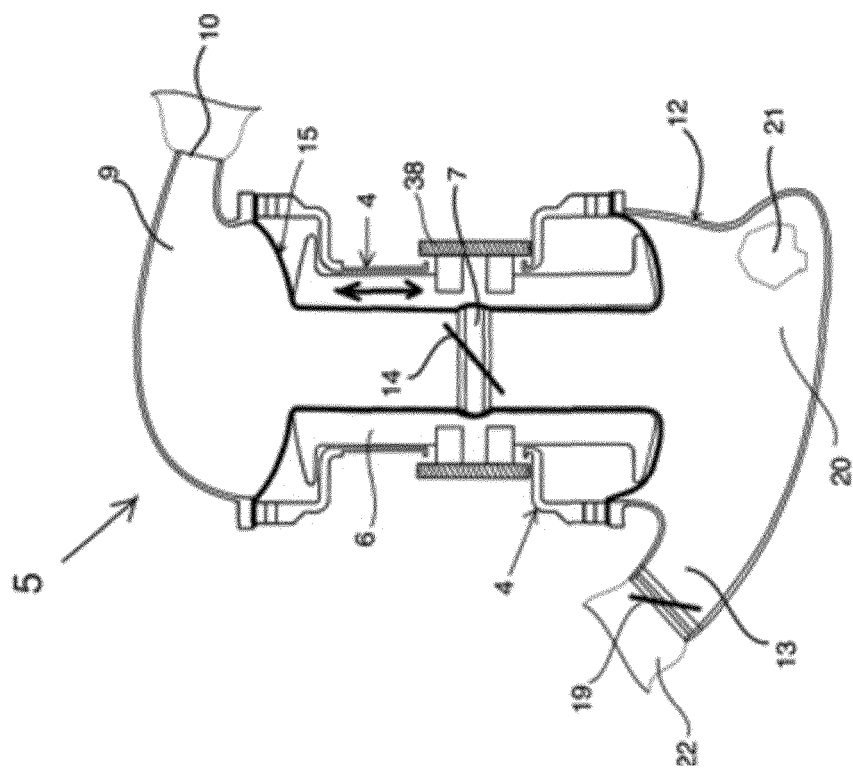
FIG. 15 is a view of a two-chambered blood pumping device as described herein.
Figure 15:
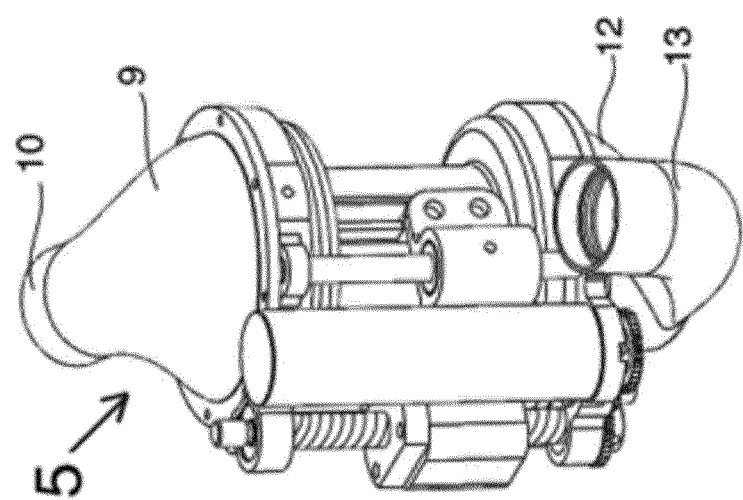

A blood pumping device 5 having two chambers is disclosed in FIG. 15. The two-chambered blood pumping device 5 comprises a pump, and a pump actuating means for inducing a blood flow in a body's circulatory system. The general design of a blood pumping device 5 having two chambers will now be described in detail.

The pump of the two-chambered blood pumping device 5 comprises an upper chamber 9 and a lower chamber 12 (see FIG. 15). The upper chamber 9 has an inlet channel 10 which allows blood to enter the upper chamber 9. Said upper chamber corresponds to an atrium of the natural heart. The lower chamber 12 is provided with an outlet channel 13 which allows blood to exit the lower chamber 12. Said lower chamber 12 corresponds to a ventricle of the natural heart.

The upper and lower chambers 9, 12 are separated by a movable valve plane 7. The valve plane corresponds to the atrioventricular (AV) plane (i.e. the plane of fibrous tissue) between the atrium and ventricle of a natural heart. A valve 14 is arranged in the valve plane 7, which corresponds to the tricuspid valve or the mitral valve depending on whether the pump is used to circulate blood in the pulmonary or aortic circuit.

The bottom part of the lower chamber 12 is advantageously designed to have a shape that is similar to the anatomic shape of the ventricles in the natural heart. In the two-chambered blood pumping device 5 the bottom part of the lower chamber 12 has a bag-like portion 20 designed to mimic the internal shape of the ventricle in a natural heart (see FIG. 3). The blood flow (Arrow) which passes from the upper chamber 9 through the valve 14 and into the lower chamber 12, hits a stopping surface 21 at the bottom part of the bag-like portion 20 and comes to a sudden stop, at which the flow abruptly changes direction and continues along the outlet channel 13. The turn at the inside of the bag-like portion 20 forms a bend of approximately 90-340°, more preferably between 100-300°, more preferably between 105-200°, and most preferably a bend between 110-150°, which is similar to the bend inside the ventricle of a natural heart. Thereafter the blood continues into the outlet channel 13.

The cross section of the bag-like portion 20 at the bottom part of the lower chamber 12 advantageously has a triangular shape (see FIG. 3a) to enable an optimal flow of blood from the lower chamber 12 into the outlet channel 13. As in a natural heart, the triangular shaped cross section facilitates the formation of flow channels inside the cavity of the lower chamber 12, such that blood will arrive from different angles at the stopping surface 21 of the bag-like portion 20, stop, change direction, enter the outlet channel 13 and subsequently leave the two-chambered blood pumping device 5 through the outlet valve 19. Alternatively the cross section of the inside construction of the lower chamber 12 may have an oval (FIG. 3b) or circular cross section (FIG. 3c).

The inner walls of the lower chamber 12, as well as the outlet channel 13 are advantageously provided with a rough surface to simulate the trabeculae carneae i.e. the muscular ridges that crisscross and project from the inner walls of the ventricles of a natural heart. Said rough surface is covered by ridges and protrusions which protrude approximately 0.01-3 mm, preferably at least 0.5-3 mm from the lower chamber 12 surface. The inner walls of the lower chamber 12 and the outlet channel 13 may also be smooth. The outlet channel 13 from the lower chamber 12 may also have a diameter which decreases continuously similarly to the design of the outlet of a ventricle in a natural heart (see FIG. 4).

To prevent leaking of blood from the two-chambered blood pumping device 5, the insides of the upper and lower chambers 9, 12 are provided with a flexible lining 15 made from a flexible plastic or rubbery material (FIG. 5). The flexible lining 15 may also be comprised of two or more layers of membrane material to improve its strength. The flexible lining 15 is advantageously made from a biocompatible material like silicone, polyurethane or another biocompatible material.

Advantageously the pump 2 of the two-chambered blood pumping device 5 further comprise one internal cylinder 6 provided with a valve plane 7, and one external cylinder 4, wherein the internal cylinder 6 is movably arranged inside the external cylinder 4. In this embodiment the upper and lower chambers 9, 12 which are separated by the valve plane 7 are housed inside the internal cylinder 6. The upper part of the internal cylinder 6 forms the upper chamber 9 corresponding to an atrium of the natural heart, and the lower part of the internal cylinder 6 forms the lower chamber 12 and corresponds to a ventricle of the natural heart. The valve plane 7 corresponds to the atrioventricular (AV) plane (i.e.

the plane of fibrous tissue) between the atrium and ventricle of a natural heart. Said valve plane 7 is provided with a valve 14 corresponding to the tricuspid valve or the mitral valve depending on whether it is located in a pump which acts in the pulmonary circuit or in the aortic circuit.

The internal cylinder 6 with the valve plane 7 is movably arranged inside the external cylinder 4, such that a pumping action is created when the internal cylinder 6 with its valve plane 7 moves linearly in the downward and upward direction inside the external cylinder 4. When the internal cylinder 6 moves in the upward direction, the valve 14 located in the valve plane 7, opens up and blood flows from the upper chamber 9 through the valve 14 and into the lower chamber 12. When the internal cylinder 6 moves in the downward direction, the valve 14 closes and the blood collected in the lower chamber 12 ejects out through the outlet channel 13. It is thus the upward and downward movements of the internal cylinder 6 with its valve plane 7 which create the pumping function of the two-chambered blood pumping device 5.

The internal and external cylinders 6, 4 are advantageously made from a stiff material, such as e.g. a biocompatible material such as titanium, ceramics, Polytetrafluoroethylene (PTFE) coated metal, diamond coated metal or a combination thereof.

To achieve an effective and energy saving pumping function for the two-chambered blood pumping device 5 the internal cylinder 6 must move in a leak-free as well as a friction-less manner during its movement inside the external cylinder 4. Advantageously the outer wall of the internal cylinder 6 as well as the inner wall of the external cylinder 4 is provided with gliding surfaces which enables the internal cylinder 6 to move with high precision in a virtually friction- and leak-free manner (see FIG. 16). The gliding surfaces are advantageously made from e.g. a ceramic material, titanium, steel, carbon fiber or any other material that will enable the internal cylinder 6 to move inside the external cylinder 4 in an essentially leek- and friction-free manner.

The fitting of the internal cylinder 6 inside the external cylinder 4 may also be made leak-free by providing the inside of the upper and lower chambers 9, 12 with a flexible lining material 15 made from a biocompatible material like silicone, polyurethane or another biocompatible material (see FIGS. 2 and 5).

The orifice of the inlet channel 10 is provided with an inlet cuff 18 designed to be connected to either the systemic veins of the systemic circuit or the pulmonary veins from the pulmonary circuit. The inlet cuff 18 is preferably made from a biocompatible material such as such as plastic, rubber or metal, silicone, polyurethane, titanium, steel or any other biocompatible materials. Parts of the inlet cuff 18 may also advantageously be made from a vessel graft material to enable easy grafting to the veins of a subject.

The outlet channel 13 from the lower chamber 12 is advantageously provided with an outlet valve 19 as in the natural heart. The outlet valve 19 will prevent the return of blood back in to the lower chamber 12 after the blood has been ejected through the outlet channel 13. The outlet valve 19 corresponds to the aortic or pulmonary valves of the natural heart depending on whether the pump 2 acts in the pulmonary circuit or in the aortic circuit.

Figure 16:
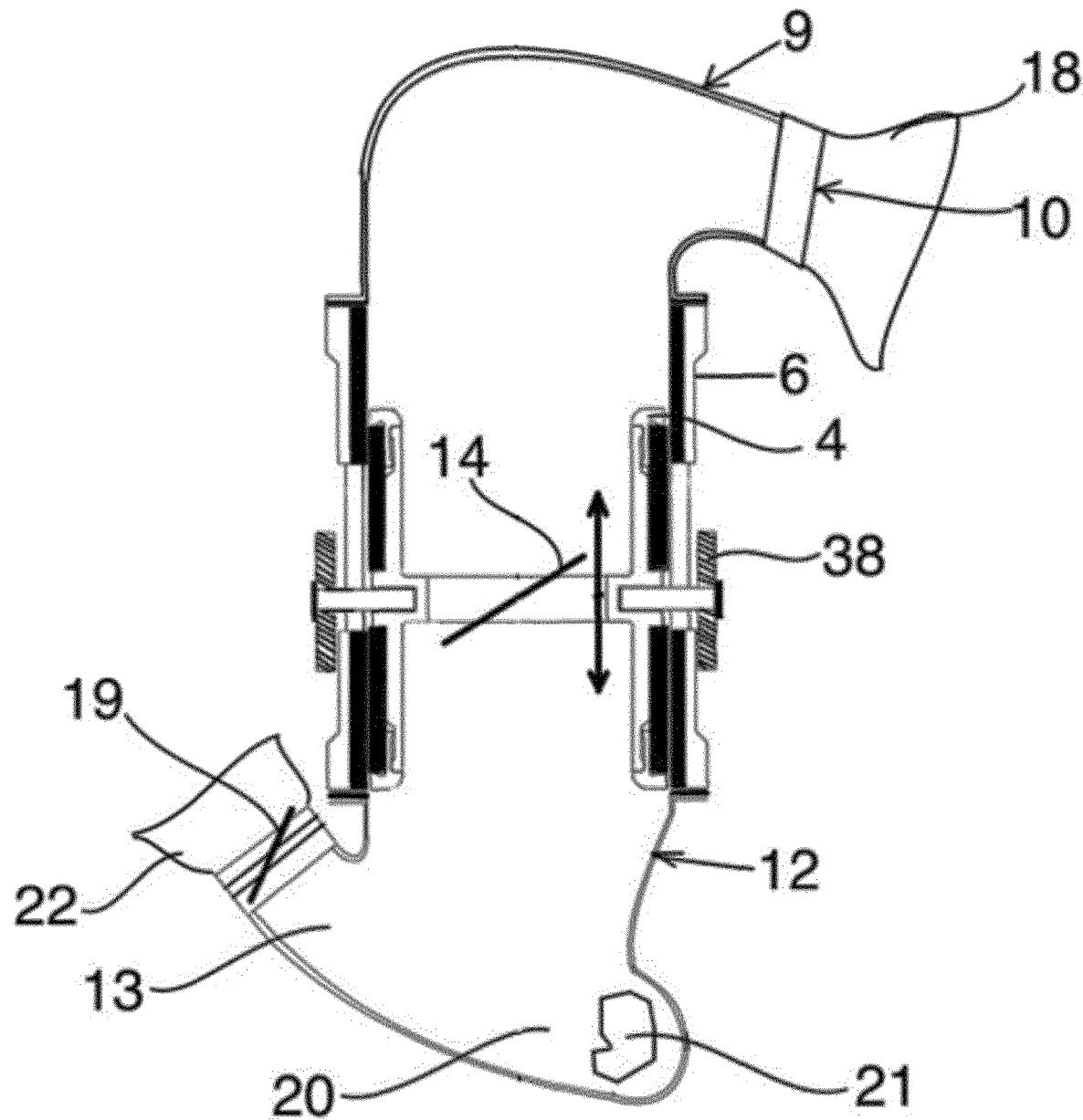
FIG. 16 shows a side view and a cross sectional view of the gliding surface provided on the outer wall of the internal cylinder and inner wall of the external cylinder in the two-chambered blood pumping device.

To facilitate the connection between the outlet channel 13 and the pulmonary artery of the pulmonary circuit or the aortic artery of the systemic circuit, the orifices of the outlet channels 13 are provided with outlet cuffs 22 which will serve as artery grafts (see FIGS. 15 and 16). Advantageously parts of the outlet cuff 22 may be made from a vessel graft material to enable easy grafting to the arteries of a subject.

A pump actuating means is configured to actuate a movement of the valve plane 7 in an upward and downward direction between said upper and lower chambers 9, 12 in response to control signals from a control unit, such that when the valve plane 7 moves in an upward direction, the valve 14 provided in the valve plane 7 is in an open position allowing a flow of blood from the upper chamber 9 to the lower chamber 12, and when the valve plane 7 moves in a downward direction the valve 14 is in the closed position and blood is ejected from the lower chamber 12 through the outlet channel 13. There are many alternative ways to accomplish the pumping movement of the two-chambered blood pumping device 5, and a number of possible embodiments of how the pump actuating means achieves this linear movement of the valve plane 7 will now be described. However the skilled person will realize that the described embodiments are not the only ways to accomplish the pumping action.

Pump Actuating Means

Use of a Driving Cylinder as a Pump Actuating Means

Figure 17:
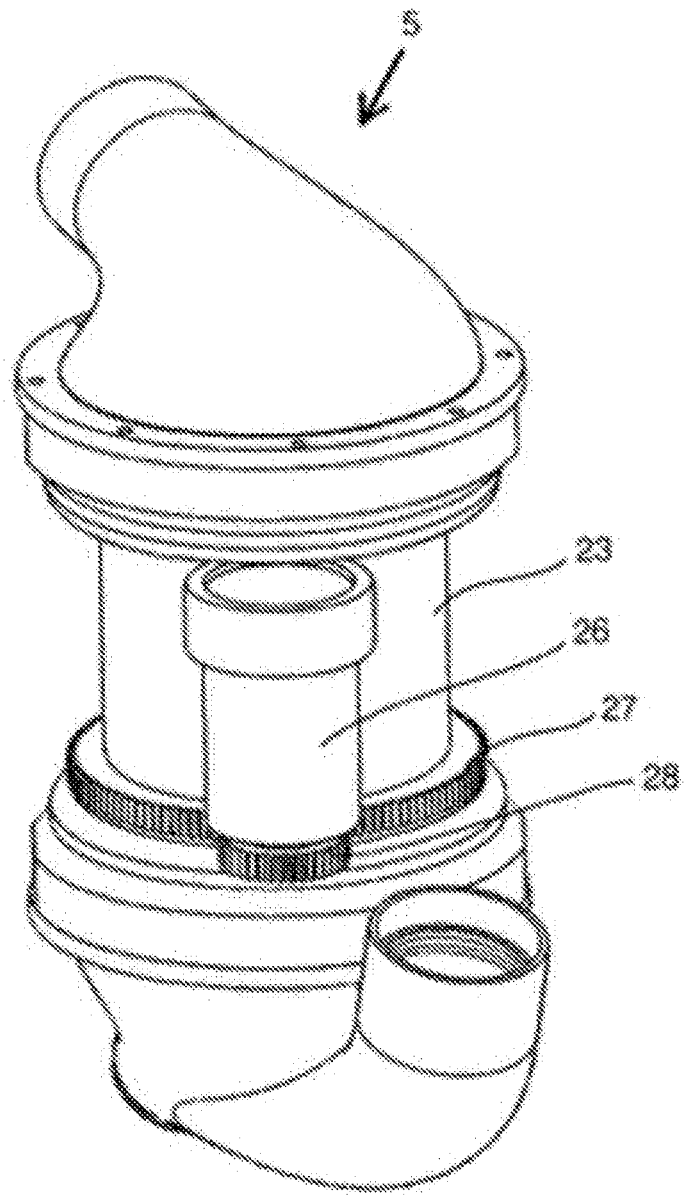
FIG. 17 shows a side view and a cross sectional view of a two-chambered blood pumping device fitted with a driving cylinder as motion generator.
Figure 17:
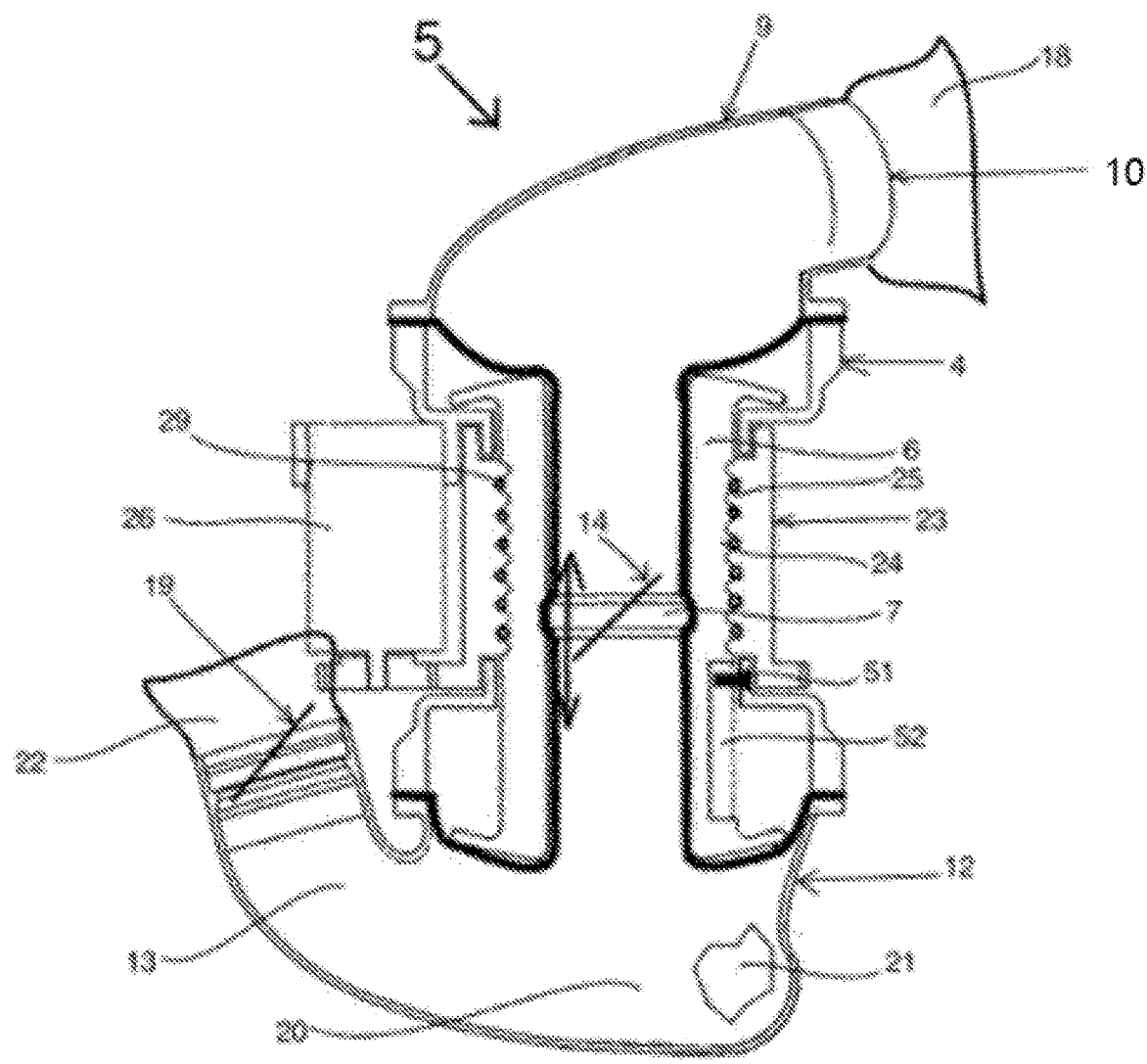

The linear movement of the internal cylinder 6 may be accomplished by means of a driving cylinder 23 as seen in FIG. 17. The outer surface of the internal cylinder 6 is provided with an external screw thread 24 arranged to cooperate with an internal screw thread 25 provided on the inside surface of the driving cylinder 23. Upon rotation of the driving cylinder 23 the internal cylinder 6 with it is valve plane 7 moves linearly either downwards or upwards inside the external cylinder 4 depending whether the driving cylinder 23 rotates in a clockwise or counter clockwise direction. This upward and downward movement of the internal cylinder 6 occurs by means of the cooperative arrangement between the external and internal screw threads 24, 25. Balls 29 may advantageously be arranged inside the internal screw thread 25 of the driving cylinder 23 to simulate a ball screw in which the rotation of the nut (driving cylinder 23) creates the linear movement of the screw which is in this construction represented by internal cylinder 6. Advantageously the balls 29 could be replaced by rollers to create a construction like a roller screw. Both the balls 29 and rollers enhance a frictionless movement of the internal cylinder 6 inside the driving cylinder 23.

The driving cylinder 23 is advantageously operated by means of one or more electromechanical motors 26. The driving cylinder 23 is advantageously also provided with an external cogwheel 27 (see FIG. 17) on its outer surface arranged to cooperate with a motor cogwheel 28 which is connected to a rotating axle of the one or more electromechanical motors 26. When the driving cylinder 23 is operated by means of an electromechanical motor 26 the motor cogwheel 28 of the electromechanical motor 26 cooperates with the external cogwheel 27 located on the outer surface of the driving cylinder 23 and alternates the rotation of the driving cylinder 23 in either the clockwise or counter clockwise direction.

Further there is at least one internal cylinder rotation-preventing member which prevents the internal cylinder 6 to be rotated by the action of the driving cylinder 23 to allow only the upward and downward movement of the internal cylinder 6. The internal cylinder rotation-preventing member may be represented by at least one rod 51 connected to the external cylinder to be extended inside a longitudinal recessed groove 52 in the wall of the internal cylinder.

Use of a Stator Cylinder as Pump Actuating Means

Figure 18:
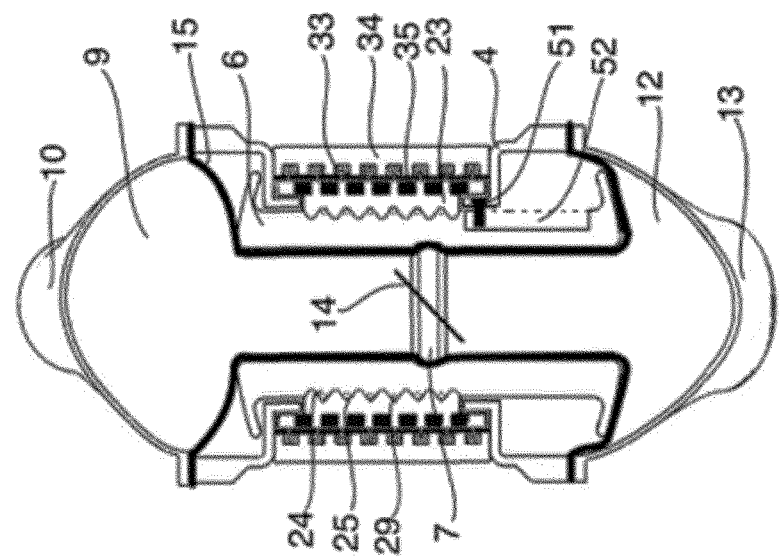
FIG. 18 shows a side view and a cross sectional view of a two-chambered blood pumping device fitted with a cylinder provided with an integrated stator coil.
Figure 18:
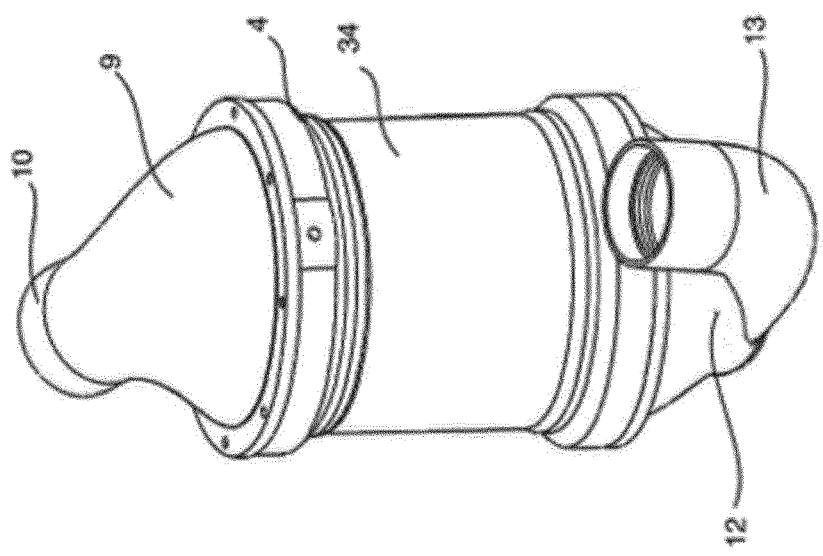

The upward and downward movements of the internal cylinder 6, i.e. the pumping function may also be accomplished by means of a cylinder with an integrated stator coil 33 (see FIG. 18). The stator coil 33 is fixed to a stator cylinder 34 which is connected to the external cylinder 4 to prevent the stator cylinder from rotating. One or more permanent magnets 35 are embedded and integrated with the outer surface of the driving cylinder 23 to enable the internal cylinder 6 to rotate when an electrical current is applied through the stator coil 33. In this embodiment the entire driving cylinder 23 functions as a rotor in an electromechanical motor 26 and thus the stator cylinder 34 together with the driving cylinder 23 works as an electromechanical motor 26. An external screw thread 24 is provided on the outer surface of the internal cylinder 6 which enables the internal cylinder 6 to be rotated into an internal screw thread 25 provided on the inside surface of the driving cylinder 23.

Upon rotation of the driving cylinder 23 the internal cylinder 6 with it is valve plane 7 moves linearly either downwards or upwards inside the external cylinder 4 depending whether the driving cylinder 23 rotates in a clockwise or counter clockwise direction. This upward and downward movement of the internal cylinder 6 occurs by means of the cooperative arrangement between the external and internal screw threads 24, 25. Balls 29 may advantageously be arranged inside the internal screw thread 36 of the driving cylinder 23 to simulate a ball screw in which the rotation of the nut (driving cylinder 23) creates the linear movement of the screw which is in this construction represented by internal cylinder 6. Advantageously the balls 29 could be replaced by rollers to create a construction like a roller screw. Both balls 29 and rollers enhance a frictionless movement of the internal cylinder 6 inside the driving cylinder 23.

When the internal cylinder 6 rotates in one direction e.g. the clockwise direction, it moves linearly in a first direction perpendicular to its rotational movement, and when the internal cylinder 6 rotates in the opposite direction e.g. the counter clockwise direction it moves linearly in a second direction perpendicular to its rotational movement and opposite to the first linear direction. The up- and down movement is accomplished by the action of the magnetic field which is created between the stator cylinder 34 and the permanent magnets 35 on the surface of the driving cylinder 23. Thus the linear movement of the internal cylinder 6 is created by the rotation of the driving cylinder 23 realized by the cooperative engagement between the external screw thread 24 on the outer wall of the internal cylinder 6 and the internal screw thread 36 provided on the internal surface of the driving cylinder 23.

Cylinder Actuating Assembly

The pump actuating means may in another advantageous embodiment comprise a cylinder actuating assembly 37 (see FIG. 19) which is connected to the internal cylinder and is powered by means of a motion generator.

Figure 19:
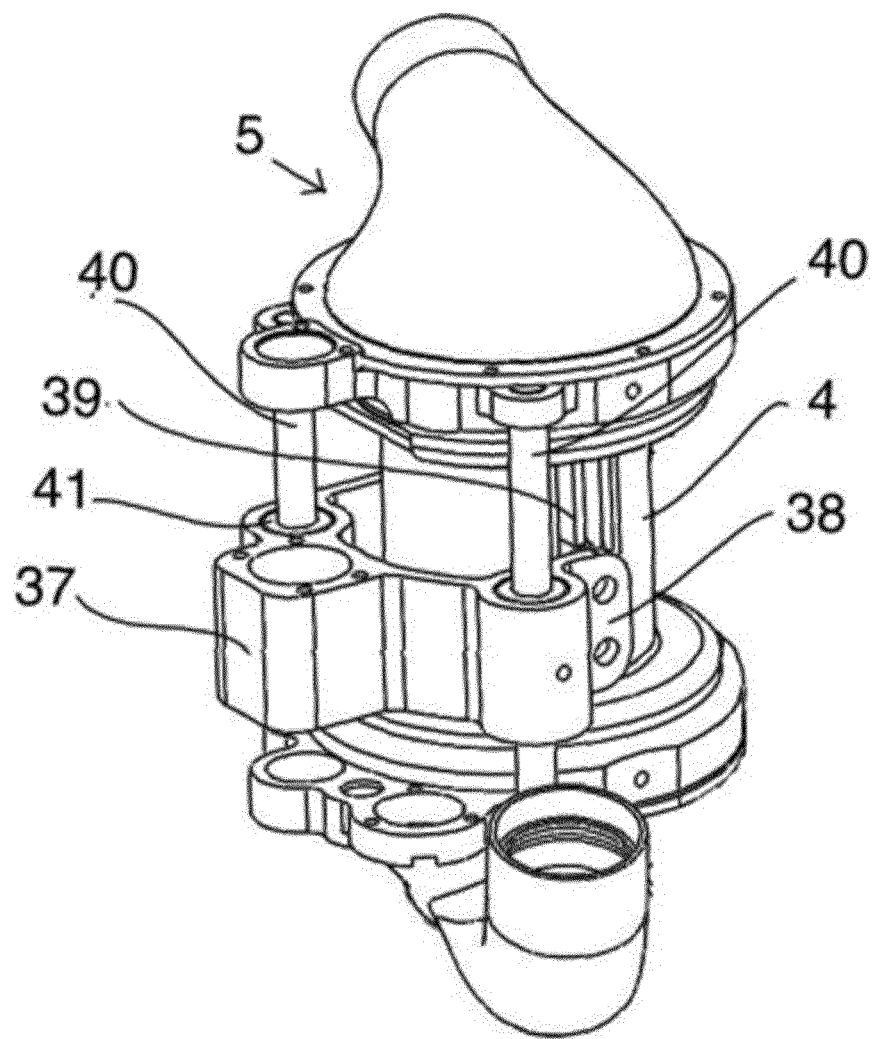
FIG. 19 is a view of a two-chambered blood pumping device fitted with a cylinder actuating assembly.

FIG. 19 shows a two-chambered blood pumping device 5 wherein the pump is provided with a cylinder actuating assembly 37. In this embodiment the cylinder actuating assembly 37 is a device which has connector arms 38 which extend around at least half of the circumference of the external cylinder 4. The external cylinder 4 is provided with rectangular openings 39 on each side through which the ends of the connector arms 38 are directly fixed to the internal cylinder 6. The shape and size of the rectangular openings 39 on each side of the external cylinder 4 are accommodated to enable the cylinder actuating assembly 37 to move the internal cylinder 6 linearly up and down inside the external cylinder 4.

The cylinder actuating assembly 37 further comprises at least two stabilizing members 40, which in an advantageous embodiment are rods which extend and run through a bearing support 41 located in each connector arm 38 of the cylinder actuating assembly 37. Said stabilizing members 40 run in parallel to the direction of movement of the internal cylinder 6. The stabilizing rods stabilize the linear up-and-down movement of the cylinder actuating assembly 37 and enable it to move along the outer wall of the external cylinder 4 with high precision. Both the stabilizing rods and the inside of the bearing support 41 are advantageously made from a friction-less material such as ceramics to enable a friction-less up-and-down movement of the pump-actuating member.

The cylinder actuating assembly 37 is powered by a motion generator to enable the movement of the internal cylinder 6 in an up-and-down movement inside the external cylinder 4.

Use of a Ball or Roller Screw as Motion Generator

In one advantageous embodiment the motion generator may be a ball or roller screw 42 or similar device. Ball screws or roller screws are mechanical linear actuators that translate rotational motion to linear motion with little friction (as described herein above).

Figure 20:
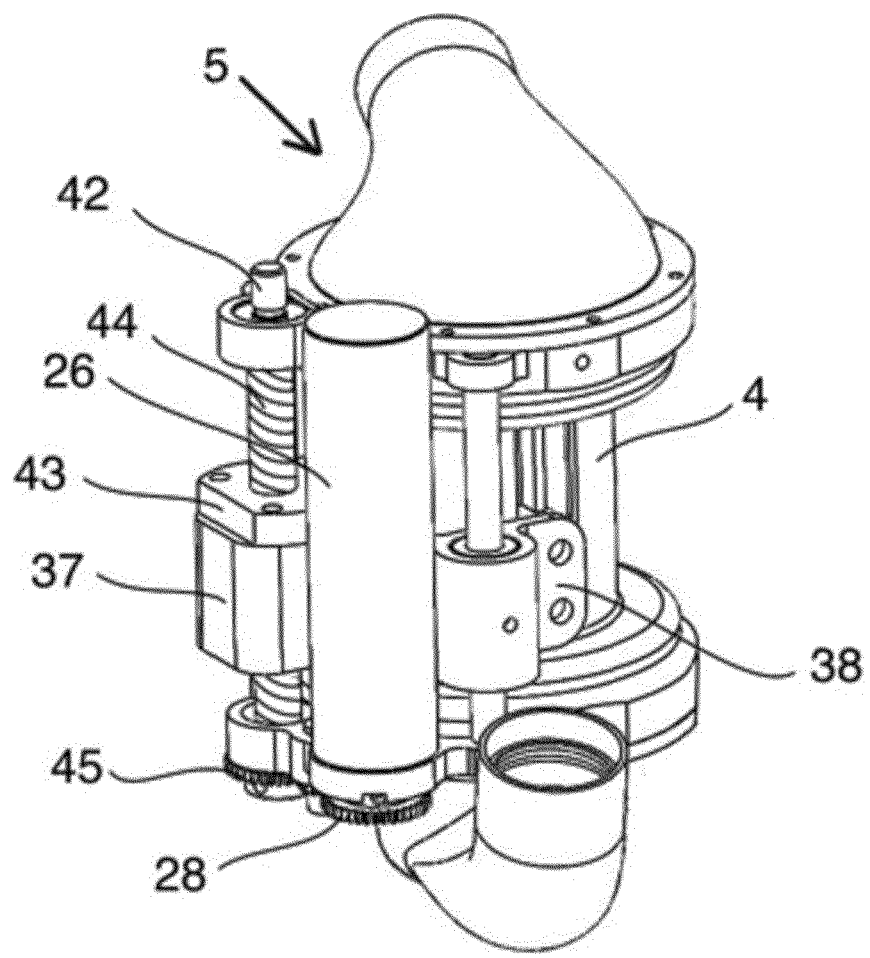
FIG. 20 is a view of a two-chambered blood pumping device fitted with a ball or roller screw as motion generator.

In the ball or roller screw 42 motion generator the ball screw or roller screw act as a linear actuator that translates a rotational motion created by power source, such as e.g. an electromechanical motor 26 into linear motion with little friction (see FIG. 20). In this embodiment the nut 43 of the ball or roller screw 42 is integrated with the cylinder actuating assembly 37 (described above), which together with its connector arms 38, extends around the external cylinder 4 and connects directly to the internal cylinder 6 through the rectangular openings 39 on each side of the external cylinder 4.

The screw 44 of the ball or roller screw 42 is advantageously provided with a cogwheel 45 in a cooperative arrangement with a motor cogwheel 28 of an electromechanical motor 26. When the electromechanical motor 26 rotates the motor cogwheel 28, said motor cogwheel 28 cooperates with the cogwheel 45 on the screw 44 of the ball or roller screw and rotates said screw 44. When the screw 44 rotates, its rotational movement is translated into a linear movement of the cylinder actuating assembly 37 i.e. the nut 43 with the connector arms 38 which moves in an upward direction or a downward direction depending on the direction of rotation of the electromechanical motor 26.

When the electromechanical motor 26 rotates the screw 44 of the ball or roller screw 42 in a first direction, the cylinder actuating assembly 37 (and the internal cylinder 6) moves in a first linear direction along the screw 44 of the ball or roller screw 42. When the electromechanical motor 26 rotates the screw 44 of the ball or roller screw 42 in a second direction, the cylinder actuating assembly 37 (and the internal cylinder 6) moves in a second linear direction along the screw 44 of the ball or roller screw 42. Said second direction is opposite to the first direction. The electromechanical motor 26 alternates its rotation between the first and the second rotation, thereby enabling the up-and-down pumping motion of the internal cylinder 6.

Use of a Hydraulic or Pneumatic Pumping System as Motion Generator

Figure 21:
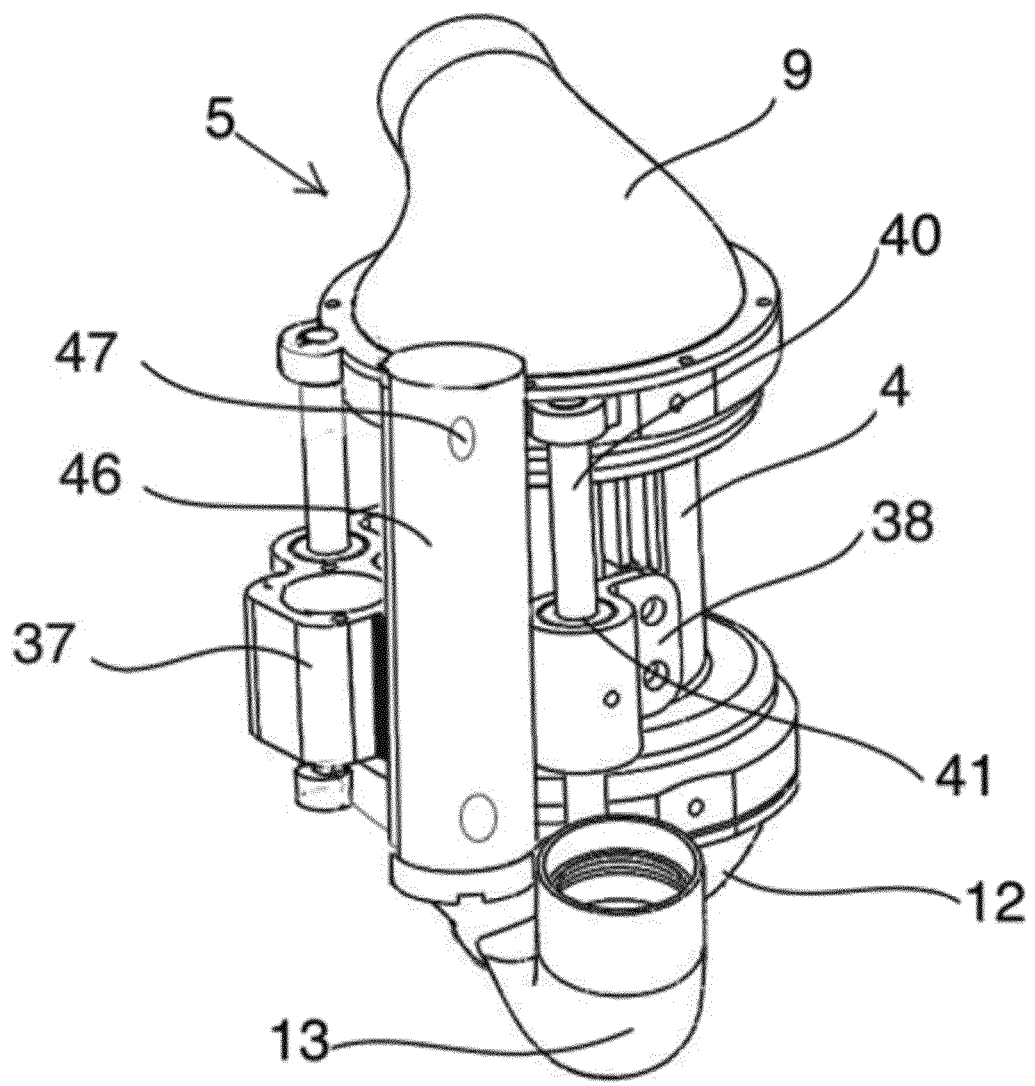
FIG. 21 is a view of a two-chambered blood pumping device fitted with a hydraulic or pneumatic pumping system.

In an alternative embodiment the motion generator may be a hydraulic or pneumatic pumping system which when connected to an internal cylinder 6 by means of a cylinder actuating assembly 37 (as described herein) enables the up-and-down movement of the internal cylinder 6 inside the external cylinder 4 (see FIG. 21).

A hydraulic cylinder (also called a linear hydraulic motor) is a mechanical actuator that is used to give a unidirectional force through a unidirectional stroke (see description above). In this embodiment the upward and downward linear movements of the internal cylinder 6 are created by the pushing and pulling action of a hydraulic or pneumatic cylinder 46 (see FIG. 21). The cylinder rods (not shown) of the hydraulic or pneumatic pumping cylinders 46 are directly connected to the cylinder actuating assembly 37 and the two connector arms 38 of the cylinder actuating assembly 37 extend around at least part of the circumference of the external cylinder 4 to connect to opposite sides of the internal cylinder 6 through rectangular shaped openings 39 in the wall of the external cylinder 4. When the hydraulic or pneumatic cylinder 46 operates, i.e. when the piston rod inside the hydraulic or pneumatic cylinder 46 moves in and out, the cylinder actuating assembly 37 moves simultaneously with the piston rod and thereby enables the up-and-down movement of the internal cylinder 6 inside the external cylinder 4.

The hydraulic cylinder 46 is operated by a hydraulic pump (not shown) provided e.g. inside the abdomen of the subject, or alternatively outside the subject. A hydraulic tube (not shown) connects the hydraulic pump to the hydraulic cylinder 46 via two connections nipples 47 provided on the hydraulic cylinder 46 to transport the hydraulic oil between the hydraulic pump and hydraulic cylinder 46. The pneumatic cylinder is powered by compressed gas supplied by an external source.

Pumping Action of the Two-Chambered Heart

Figure 22:
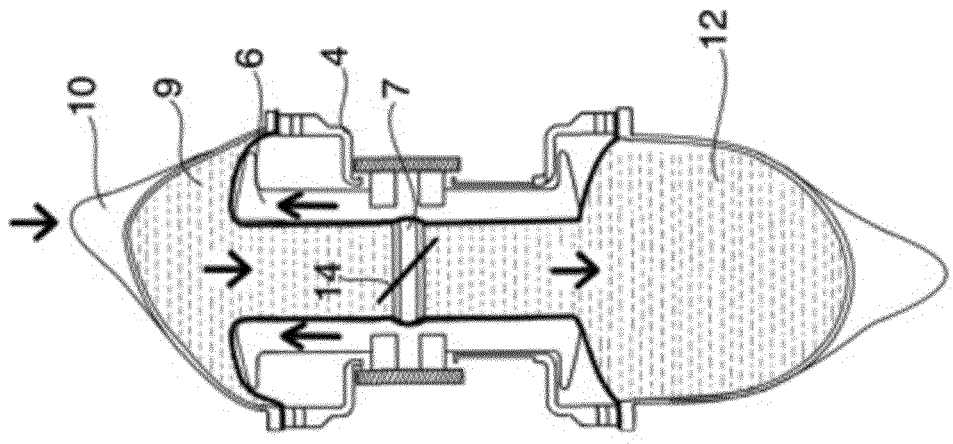
FIG. 22 is a cross sectional view of the two-chambered blood pumping device showing how the internal cylinder moves upwards and blood flows from the upper chamber through the open valve and into the lower chamber.
Figure 23:
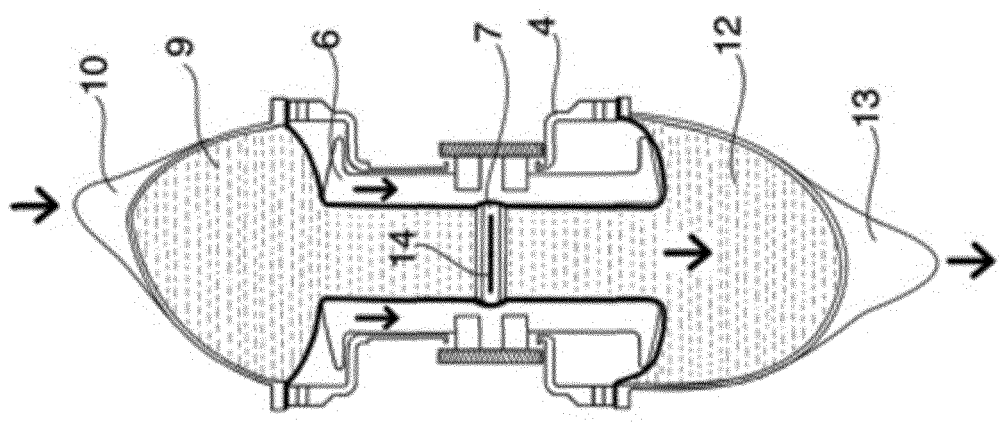
FIG. 23 is a cross sectional view of the two-chambered blood pumping device showing how the internal cylinder moves downwards ejecting blood from the lower chamber through the outlet channel.

The pumping action of the two-chambered heart will now be described (see FIGS. 22 and 23).

Blood enters the upper chamber 9 of the two-chambered blood pumping device 5 through the inlet channel 10. In one pump motion cycle blood arrives from the systemic circuit to enter the pump 5 if the two-chambered blood pumping device 5 is connected to the pulmonary artery or alternatively, oxygenated blood arrives from the pulmonary circuit to enter the pump if the two-chambered blood pumping device 5 is connected to the aorta. When the upper chamber 9 has been filled with blood, the valve 14 located in the valve plane 7 of the internal cylinder 6 switches to an open position when the internal cylinder 6 moves upwards in a first linear direction inside the external cylinder 4 (see FIG. 22). When the internal cylinder 6 moves upwards, blood collected in the upper chamber 9 flows through the open valve 14 located in the valve plane 7 and into the lower chamber 12. The linear movement of the internal cylinder 6 may be realized as described elsewhere in this document.

After the lower chamber 12 has filled with blood, the valve 14 located in the valve plane 7 closes. The internal cylinder 6 thereafter moves downwards in a second linear direction opposite to the first direction, inside the external cylinder 4, and pushes the blood towards the bottom part of the lower chamber 12, (see FIG. 23). When the blood is pushed towards the bottom of the lower cylinder 12 it enters the bag-like portion 20 and hits the stopping surface 21, stops, changes direction and exits the lower chamber 12 through the outlet channel 13. The outlet valve 19 located at the orifice of the outlet channel opens during the outflow of blood, and thereafter closes to prevent blood from re-entering the lower chamber 12 through the outlet channel 13, (see FIG. 3).

Use of the Two-Chambered Blood Pumping Device as a Heart Assist Device

The two-chambered blood pumping device may advantageously be used as a heart assist device in a subject who has a partially diseased heart, such as e.g. a malfunctioning ventricle. The device takes blood from a diseased ventricle of the heart and helps pump it to the aorta if the diseased part of the heart is the left ventricle or to the pulmonary artery if the diseased ventricle is the right ventricle.

The inlet cuff 18 of the two-chambered blood pumping device 5 is connected to the diseased ventricle by means of a vessel graft. A first end of said inlet cuff 18 is advantageously made from a wide strip of vessels graft tissue which surrounds the inlet channel 10 of the upper chamber 9 which is sutured to the ventricle. The second end of the inlet cuff 18 is advantageously fitted with a fast connection such as a blocking stripe made from glass fiber reinforced silicone or other material used for this purpose or other fast connection can be used. Said fast connection connects to the inlet channel 10 of the two-chambered blood pumping device 5. Alternatively, the collar cuff 18 may be glued directly to the inlet channel 10 of the two-chambered blood pumping device 5. The outlet channel 13 of the two-chambered blood pumping device 5 is connected to the aortic or pulmonary artery respectively by means of suturing to an outlet cuff 22 which also advantageously is made from a vessel graft material. Advantageously also the outlet cuff 22 is fitted with a fast connection such as a blocking stripe made from glass fiber reinforced silicone or other material used for this purpose or other fast connection can be used. Said fast connection connects to the outlet channel 13 of the two-chambered blood pumping device 5. Alternatively, the outlet cuff 22 may be glued to the outlet channel 13 of the two-chambered blood pumping device 5.

After the two-chambered blood pumping device 5 has been placed in position in e.g. the abdominal cavity the inlet cuff 18 needs to penetrate the diaphragm to be connected to either left or right ventricle.

The energy to power the pump actuating means of the two-chambered blood pumping device 5 may be supplied by an external source via a cable through the skin or by means of induction or ultra sound, or alternatively by an implanted battery. The implanted battery may be recharged from the outside by an external source via a cable or by means of induction or ultra sound.

The energy to power the pump actuating means is supplied by an implantable rechargeable battery (not shown) or by an external energy source 60 such as e.g. rechargeable batteries placed around the waist or included in a jacket worn by the subject. The external energy source 60 gives the required power directly to the pump actuating means and to the implanted battery to be recharged via a cable or by means of induction or ultra sound. If for some reason the subject for a short period removes the external energy source 60, e.g. to take a shower, the internal battery will supply the pump actuating means with enough energy for a short period of time.

The pump actuating means is advantageously controlled by an implanted micro-computer 70 or electronic chips 70. The input information to the computer is advantageously provided from the sinus node (which remains inside the body after removing the diseased heart), via pacemaker-type electrodes. However, the micro-computer 70 or electronic chips 70 may also receive signals from pressure sensors placed around major arteries. When the patient changes his physical activities the blood pressure will reflect the situation. The micro-computer 70 or the electronic chips 70 will send information to the pump actuating means to change its pumping activity accordingly. If for some reason the microcomputer 70 or electronic chips 70 are not receiving any input information, the pump actuating means will continue at a constant level of activity, and instead the patient will have to adjust his physical activities. The body temperature, which increases with physical activity, may also be used to activate the pump actuating means during high physical efforts.

Use of the Two-Chambered Blood Pumping Device as a Cardiopulmonary Bypass

Figure 24:
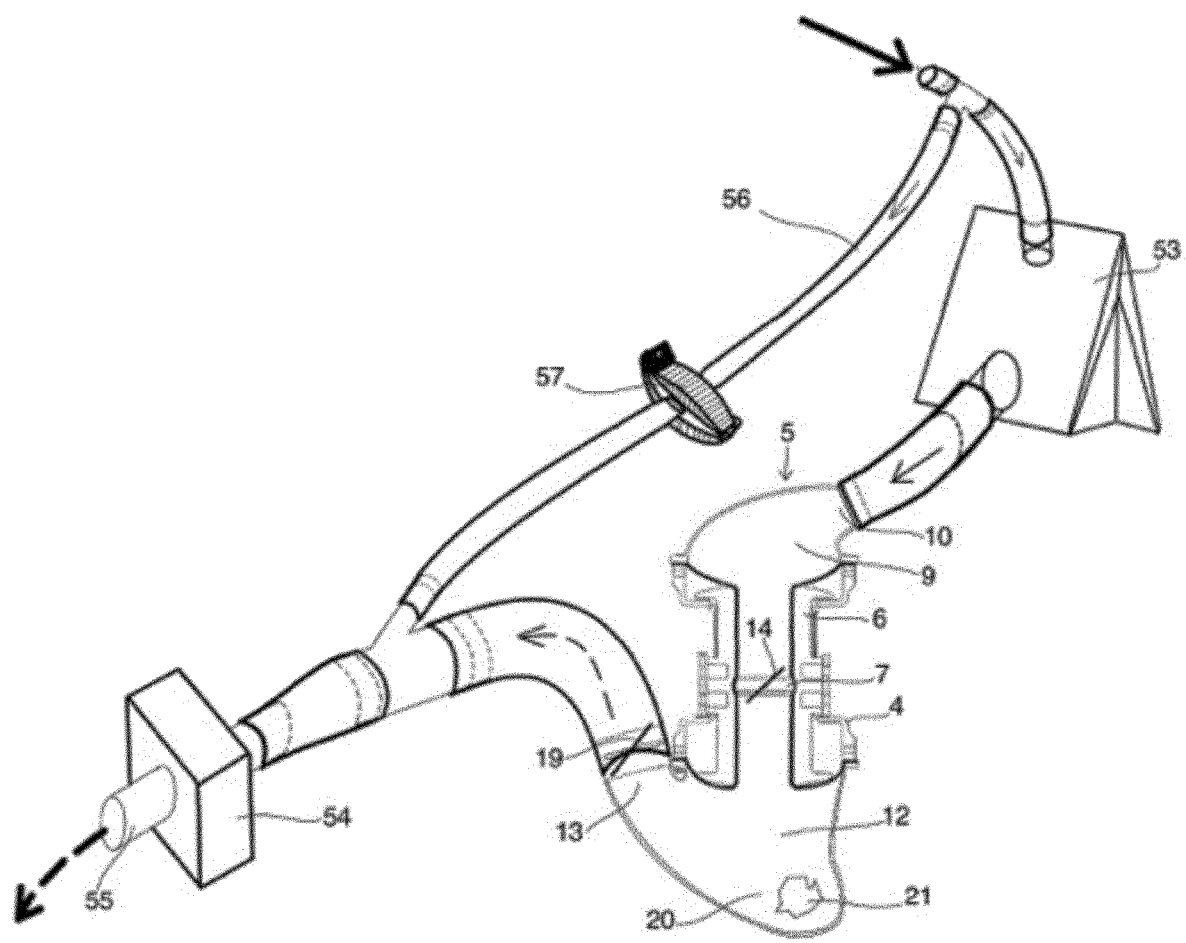
FIG. 24 shows a CPB complementary unit comprising the two-chambered blood pumping device when inserted in the arterial line of the CPB.

The two-chambered blood pumping device may be used as a cardiopulmonary bypass (CPB) complementary pump during surgery on a subject. As can be seen in FIG. 24 a CPB unit comprises an expandable reservoir, the two-chambered blood pumping device 5, a blood filter and a security shunt system.

Typically when using the Heart-Lung machine, blood is drained from the body by placing a cannula in the right atrium, vena cava, or femoral vein to a reservoir. Venous blood that is removed from the body by the cannula is filtered, cooled or warmed, oxygenated in an oxygenator or gas-exchanger and returned to the body. The cannula which is used to return the oxygenated blood is usually inserted in the ascending aorta, but it may also be inserted in the femoral artery.

The CPB complementary unit (as described in this document) comprising the two-chambered blood pumping device 5 is inserted in the arterial line of the CPB (FIG. 24). Blood is withdrawn from the body by placing a cannula in the right atrium, vena cava as described above, and thereafter it is oxygenated in the oxygenator or gas exchanger. Oxygenated blood (straight bold Arrow in FIG. 24) which returns from the heart-lung machines roller pump is connected to the expandable, sterile, reservoir bag 53 which serves as a security bag and buffers any possible difference in the output between the CPB (heart-lung machine) roller pump and the two-chambered blood pumping device 5. The réservoir bag 53 is connected to the inlet channel 10 of the two-chambered blood pumping device 5. The reservoir bag 53 is advantageously placed at a higher position than the two-chambered blood pumping device 5 to allow the blood to enter the upper chamber 9 by means of gravity. When the upper chamber 9 has been filled with blood, the valve 14 located in the valve plane 7 of the internal cylinder 6 switches to an open position when the internal cylinder 6 moves upwards in a first linear direction inside the external cylinder 4. When the internal cylinder 6 moves upwards, blood collected in the upper chamber 9 flows through the open valve 14 located in the valve plane 7 and into the lower chamber 12. The linear movement of the internal cylinder 6 may be realized as described elsewhere in this document.

After the lower chamber 12 has filled with blood, the valve 14 located in the valve plane 7 closes as the internal cylinder 6 moves downwards in a second linear direction opposite to the first direction, inside the external cylinder 4, and pushes the blood towards the bottom part of the lower chamber 12. When the blood is pushed towards the bottom of the lower chamber 12 it enters the bag-like portion 20 and hits the stopping surface 21, stops, changes direction and exits the lower chamber 12 through the outlet channel 13. The outlet valve 19 located at the orifice of the outlet channel opens during the outflow of blood, and thereafter closes to prevent blood from re-entering the lower chamber 12 through the outlet channel 13.

As explained above the pumping mechanism of the two-chambered blood pumping device 5 is achieved by up and downward movement of the internal cylinder which causes the blood to leave the two-chambered blood pumping device 5 with a pulsatile flow. The blood passes through a filter 54 and is thereafter injected (dashed bold arrow in FIG. 23) to the ascending aorta or femoral artery by a connecting cannula 55. As seen in FIG. 24 the CPB complementary unit has a security/emergency shunt 56 such that if anything fails one can continue the cardiopulmonary bypass in the usual manner with non-pulsatile flow as provided by the heart-lung machines roller pump. The flow through the security shunt system can be controlled by a clamp 57.

The invention claimed is:

1. A blood pumping device comprising
   at least a first pump, and
   at least a first pump actuator for inducing a blood flow in a body's circulatory system,
   said pump comprising one upper chamber having an inlet channel and one lower chamber having an outlet channel, said upper and lower chambers are separated by a movable valve plane provided with a valve and said pump actuator is configured to apply a force inducing a movement to said valve plane in an upward and downward direction between said upper and lower chambers in response to control signals from a control unit, such that when said valve plane moves in an upward direction, the valve provided in the valve plane is in an open position allowing a flow of blood from the upper chamber to the lower chamber, and when the valve plane moves in a downward direction the valve is in the closed position and blood is ejected from the lower chamber through the outlet channel,
   characterized in that the lower chamber is provided with a bag portion at a bottom part of the lower chamber between the valve and the outlet channel, wherein an inner surface of the bag portion defines a stopping surface at a bottom of the bag portion, wherein the bottom of the bag portion has a shape that:
   makes a turn of between 110° to 150° to cause blood entering the lower chamber to hit the stopping surface and come to a sudden stop, wherein the turn causes the flow of blood along the inner surface of the bag portion to abruptly change; and directs blood at the stopping surface to continue flowing along the outlet channel.

2. The blood pumping device according to claim 1, wherein a cross-section of the bag portion has a triangular shape, an oval shape, or a circular shape.

3. The blood pumping device according to claim 1, wherein the outlet channel has a decreasing diameter.

4. The blood pumping device according to claim 1, wherein inner walls of the lower chamber and the outlet channel have a rough inner surface.

5. The blood pumping device according to claim 1, wherein the upper and lower chambers are provided with a flexible lining material.

6. The blood pumping device according to claim 1, wherein the outlet channel is provided with an outlet valve.

7. The blood pumping device according to claim 1, wherein the pump further comprises, one internal tube provided with said valve plane and valve, and one external tube, said internal tube is movably arranged inside the external tube, and said pump actuator is configured to apply a force inducing a movement to said internal tube in an upward and downward direction in response to control signals from said control unit, such that when the internal tube moves in an upward direction inside the external tube, the valve provided in the valve plane is in an open position allowing a flow of blood from the upper chamber to the lower chamber, and when the internal tube moves in a downward direction inside the external tube the valve is in the closed position and blood is ejected from the lower chamber through the outlet channel.

8. The blood pumping device according to claim 7, wherein the outer wall of the internal tube and inner wall of the external tube are provided with gliding surfaces.

9. The blood pumping device according to claim 7, wherein the pump actuator is a driving cylinder provided with an external cogwheel and an internal screw thread, said external cogwheel is arranged to cooperate with a motor cogwheel of an electromechanical motor, and said internal screw thread is arranged to cooperate with an external screw thread provided on the outside of the internal tube.

10. The blood pumping device according to claim 7, wherein the pump actuator is a stator cylinder provided with an internal screw thread arranged to cooperate with an external screw thread provided on the internal tube, said cooperative arrangement enables the internal tube to move linearly up and down inside the stator cylinder.

11. The blood pumping device according to claim 7, wherein the pump actuating member is a cylinder actuator assembly connected to the internal tube and powered by means of a motion generator to enable a linear up-and-down motion of the internal tube inside the external tube.

12. The blood pumping device according to claim 11, wherein the motion generator is a hydraulic or pneumatic cylinder which when connected to the internal tube by means of a cylinder actuator assembly enables the up-and-down movement of the internal tube inside the external tube.

13. The blood pumping device according to claim 11, wherein the motion generator is a ball screw or a roller screw which translates a rotational motion provided by a rotational power source into a linear up-and-down motion of the internal tube inside the external tube.

14. The blood pumping device according to claim 1, wherein energy to power the pump actuator is supplied by an implantable rechargeable battery or by an external energy source.

15. The blood pumping device according claim 14, wherein an external energy source gives required power directly to the pump actuator and to the implantable rechargeable battery to be recharged via a cable or by means of induction or ultra sound.

16. The blood pumping device according to claim 1, wherein the pump actuator is controlled by an implanted microcomputer or electronic chips.

17. The blood pumping device according to claim 1, wherein the blood pumping device comprises a second pump and a second pump actuator.

18. The blood pumping device according to claim 1, wherein the blood pumping device is provided with at least one additional pump actuator which functions independently of the first pump actuator.

* * * * *